US008676298B2

(12) United States Patent
Wang et al.

(10) Patent No.: US 8,676,298 B2
(45) Date of Patent: Mar. 18, 2014

(54) MEDICAL IMAGE ALIGNMENT APPARATUS, METHOD, AND PROGRAM

(75) Inventors: Caihua Wang, Tokyo (JP); Keigo Nakamura, Tokyo (JP); Satoshi Ihara, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 157 days.

(21) Appl. No.: 13/219,166

(22) Filed: Aug. 26, 2011

(65) Prior Publication Data

US 2012/0053454 A1 Mar. 1, 2012

(30) Foreign Application Priority Data

Aug. 30, 2010 (JP) .................................. 2010-191785
Aug. 30, 2010 (JP) .................................. 2010-192509

(51) Int. Cl.
*A61B 6/03* (2006.01)
(52) U.S. Cl.
USPC ........... 600/425; 600/407; 600/411; 600/426; 600/427
(58) Field of Classification Search
USPC ........................... 600/407, 410, 411, 426, 427
See application file for complete search history.

(56) References Cited

U.S. PATENT DOCUMENTS

| | | | |
|---|---|---|---|
| 5,732,703 A * | 3/1998 | Kalfas et al. ................... | 600/407 |
| 6,381,485 B1 * | 4/2002 | Hunter et al. ................. | 600/407 |
| 6,470,207 B1 * | 10/2002 | Simon et al. ................... | 600/426 |
| 7,974,677 B2 * | 7/2011 | Mire et al. ..................... | 600/407 |

FOREIGN PATENT DOCUMENTS

| | | |
|---|---|---|
| JP | 6215153 A | 8/1994 |
| JP | 2005287731 A | 10/2005 |
| JP | 2006034548 A | 2/2006 |
| JP | 2008-006187 A | 1/2008 |
| JP | 2009-207727 A | 9/2009 |
| JP | 2010131224 A | 6/2010 |

OTHER PUBLICATIONS

Japanese Office Action for Application No. 2010-191785; Feb. 7, 2012.

* cited by examiner

*Primary Examiner* — Baisakhi Roy
(74) *Attorney, Agent, or Firm* — Sughrue Mion, PLLC

(57) ABSTRACT

Generating, with respect to each of the three-dimensional image and the three-dimensional comparison image, a plurality of tomographic images orthogonal to a central axis of each vertebra of the subject along the central axis, calculating a first characteristic amount representing a profile in a direction orthogonal to the central axis at each point on the central axis based on the tomographic images, calculating a second characteristic amount representing a profile in a direction of the central axis at each point on the central axis based on the tomographic images, calculating a third characteristic amount representing regularity of disposition of each vertebra at each point on the central axis based on the calculated first and second characteristic amounts, and aligning positions of the third characteristic amount calculated from the three-dimensional image and the third characteristic amount calculated from the three-dimensional comparison image along the central axis.

10 Claims, 20 Drawing Sheets

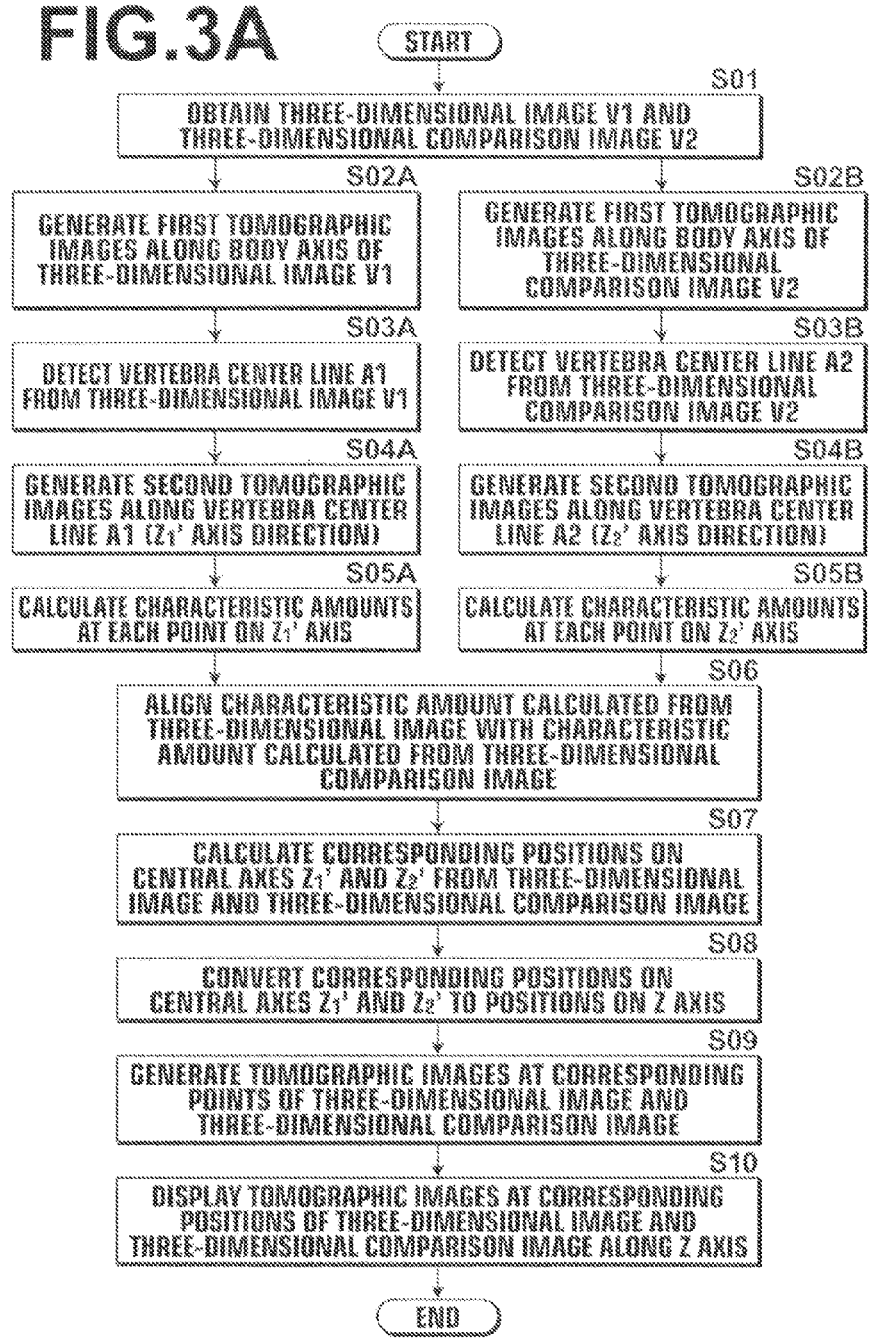

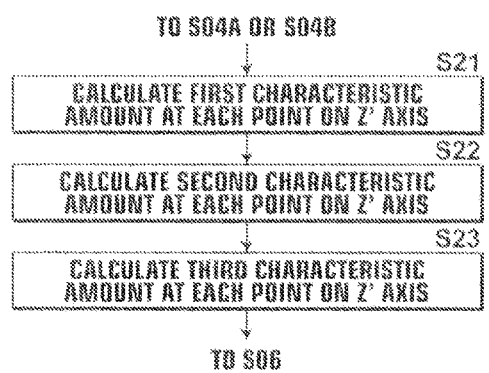

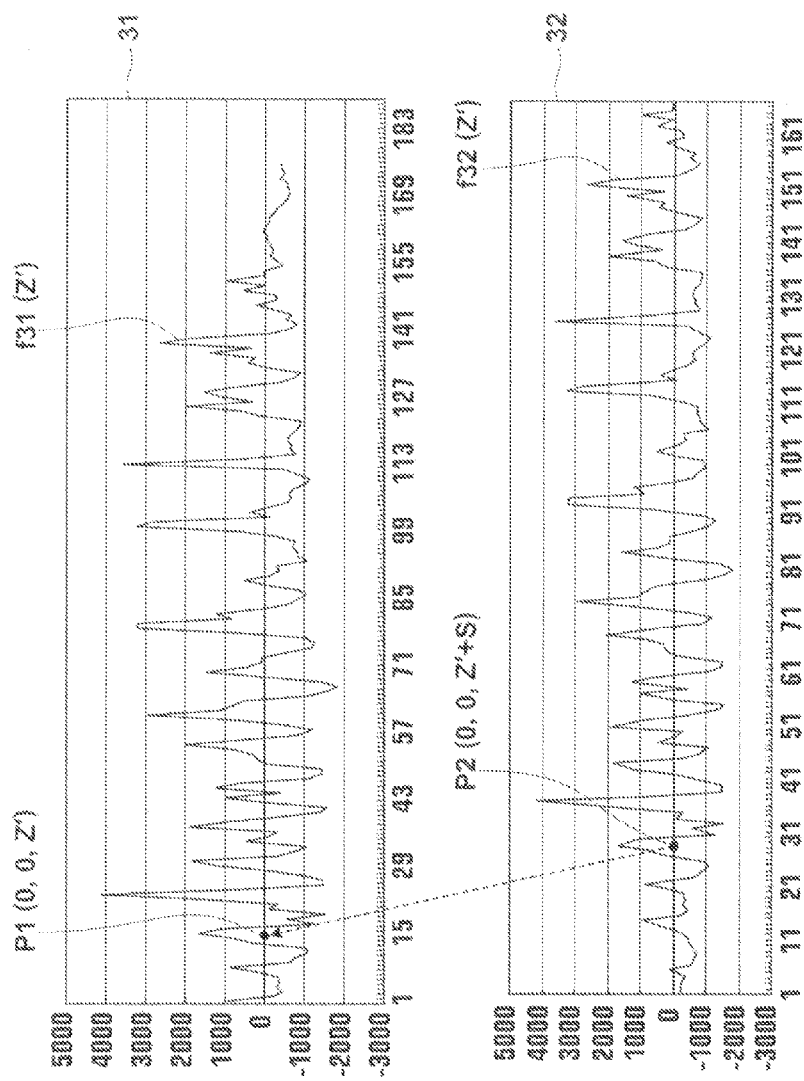

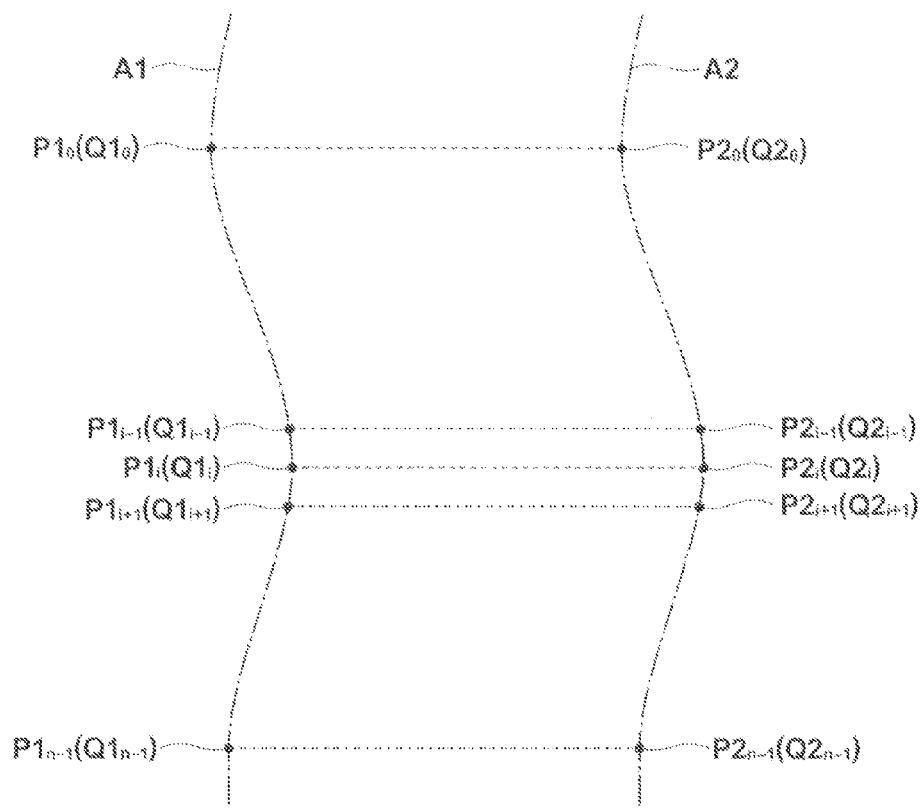

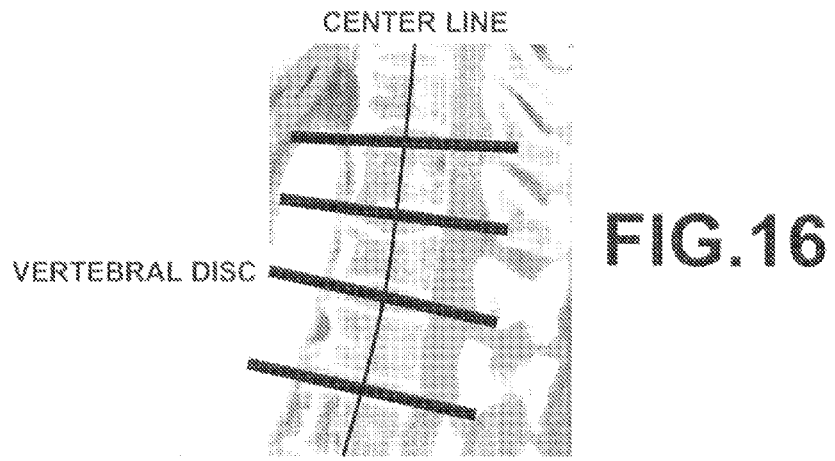
FIG.16
FIG.17
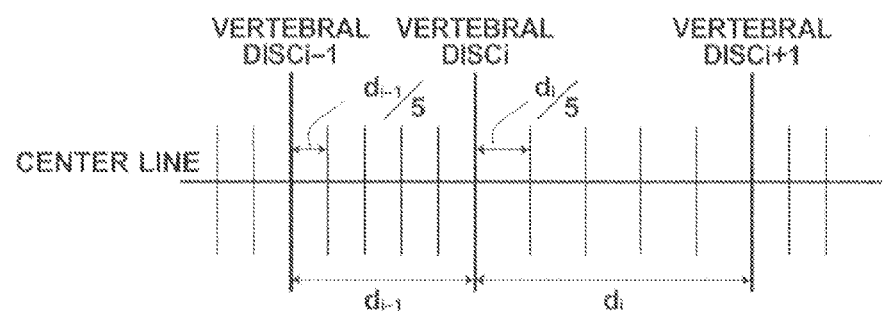

MEDICAL IMAGE ALIGNMENT APPARATUS, METHOD, AND PROGRAM

BACKGROUND OF THE INVENTION

1. Field of the Invention

The present invention relates to a medical image alignment apparatus, method, and program for determining positional correspondence relationship between a plurality of three-dimensional images which include vertebrae. The invention also relates to a cross-sectional spine image display apparatus, method, and program, and more particularly to a cross-sectional spine image display apparatus, method, and program for generating a cross-sectional image of a vertebra portion based on three-dimensional image data and displaying the generated image.

2. Description of the Related Art

When performing comparative image reading of a plurality of three-dimensional images formed of a plurality of cross-sectional images sliced in a direction orthogonal to a body axis direction, there is a demand for displaying corresponding cross-sectional images of each three-dimensional image side by side by performing site recognition and determining correspondence relationship between each cross-sectional image in each three-dimensional image based on a pair of corresponding slice positions specified by the operator, a slice thickness of each three-dimensional image, and the like.

In response to such a demand, it is conceivable that the same region may be extracted from a plurality of three-dimensional images formed of a plurality of cross-sectional images using a technology, such as that described in Japanese Unexamined Patent Publication No. 2008-006187, which recognizes an anatomical structure included in a medical image and displays an axial image of the specified region based on information of the recognized region.

In the mean time, with the recent progress in imaging devices (modalities), resolution of image data obtained by imaging devices has improved, thereby allowing detailed analysis of a subject based on the image data. For example, the multi-detector row computed tomography may obtain a plurality of tomographic images at a time, and tomographic images with a thin slice thickness may be obtained. A thinner slice thickness results in improvement in the resolution of three-dimensional data, in a body axis direction, made up of a plurality of stacked tomographic images, whereby more detailed three-dimensional image data may be obtained.

A structural analysis of a vertebra may be performed using the aforementioned three-dimensional data. For example, Japanese Unexamined Patent Publication No. 2009-207727 describes that a center line of a vertebra is obtained by analyzing three-dimensional image data. Japanese Unexamined Patent Publication No. 2009-207727 also describes that a spongy portion of each vertebral body constituting a vertebra in a body axis direction is estimated based on pixel values (voxel values) of a specific region near the center line of the vertebra, then a characteristic amount of pixel value of the specific region is calculated in estimated spongy portion of each vertebral body, a three-dimensional center of the cavernous portion of each vertebral body is detected based on the characteristic amount, and positions of both ends of each vertebral body are calculated based on the detected three-dimensional center. Further, Japanese Unexamined Patent Publication No. 2009-207727 describes that a midpoint between three-dimensional centers in spongy portions of adjacent two vertebral bodies is determined to be the intervertebral portion of the two vertebral bodies.

Use of the method described in Japanese Unexamined Patent Publication No. 2008-006187 allows recognition of which of head region, neck region, chest region, abdominal region, and leg region is represented by which of sliced images and, therefore, it is possible, for example, to extract chest axial images from a plurality of three-dimensional images. But, it is difficult to extract axial images at precisely corresponding chest positions.

Further, use of the method described in Japanese Unexamined Patent Publication No. 2008-006187 allows alignment only in a body axis direction as the method performs alignment using tomographic images orthogonal to the body axis direction. For example, the aforementioned method may not respond to the demand for performing comparative image reading with respect to a cross-section orthogonal to the center line of a specific vertebra in a past three-dimensional image and a cross-section at a corresponding position in a current three-dimensional image, as required in the examination of vertebral problems.

The present invention has been developed in view of the circumstances described above, and it is an object of the present invention to provide a medical image alignment apparatus, method, and program capable of automatically determining positional correspondence relationship between a plurality of three-dimensional medical images with high accuracy.

Further, for example, in the field of orthopedic surgery, there may be a case in which each vertical cross-section of a spine is displayed and observed using three-dimensional image data. In the display of the vertical cross-section of spine, it is conceivable that a cross-sectional image of a vertebra sliced orthogonal to the center line at the position of each vertebral disc is generated and a plurality of cross-sectional image is displayed side by side. But a region desired to be observed does not always correspond to the position of the vertebral disc displayed in cross-section. There may be a case in which the observer, such as a doctor or the like, wants to move the position of the cross-sectional image to be displayed from the position of the cross-sectional image currently displayed. But, in the display of vertebrae in cross-section, there has been no such function to adjust positions of cross-sections, and it has been possible to display only a cross-section at a fixed position.

In view of the circumstances described above, it is a further object of the present invention to provide a cross-sectional spine image display apparatus, method, and program that allows an observer to easily observe a cross-section at any position in the cross-sectional display of vertebrae.

SUMMARY OF THE INVENTION

A medical image alignment apparatus of the present invention is an apparatus for aligning a three-dimensional image which represents a subject having vertebrae with a three-dimensional comparison image which represents the subject and is compared with the three-dimensional image, the apparatus including: a three-dimensional image obtaining unit for obtaining the three-dimensional image and the three-dimensional comparison image;

an image generation unit for generating, with respect to each of the three-dimensional image and the three-dimensional comparison image, a plurality of tomographic images orthogonal to a central axis of each vertebra of the subject along the central axis;

a first characteristic amount calculation unit for calculating, with respect to each of the three-dimensional image and the three-dimensional comparison image, a first characteristic amount representing a profile in a direction orthogonal to the central axis at each point on the central axis based on the tomographic images;

a second characteristic amount calculation unit for calculating, with respect to each of the three-dimensional image and the three-dimensional comparison image, a second characteristic amount representing a profile in a direction of the central axis at each point on the central axis based on the tomographic images;

a third characteristic amount calculation unit for calculating, with respect to each of the three-dimensional image and the three-dimensional comparison image, a third characteristic amount representing regularity of disposition of each vertebra at each point on the central axis based on the calculated first and second characteristic amounts; and a vertebra alignment unit for aligning positions of the third characteristic amount calculated from the three-dimensional image and the third characteristic amount calculated from the three-dimensional comparison image along the central axis.

A medical image alignment method of the present invention is a method for aligning a three-dimensional image which represents a subject having vertebrae with a three-dimensional comparison image which represents the subject and is compared with the three-dimensional image, the method including the steps of:

Obtaining the three-dimensional image and the three-dimensional comparison image;

generating, with respect to each of the three-dimensional image and the three-dimensional comparison image, a plurality of tomographic images orthogonal to a central axis of each vertebra of the subject along the central axis;

calculating, with respect to each of the three-dimensional image and the three-dimensional comparison image, a first characteristic amount representing a profile in a direction orthogonal to the central axis at each point on the central axis based on the tomographic images;

calculating, with respect to each of the three-dimensional image and the three-dimensional comparison image, a second characteristic amount representing a profile in a direction of the central axis at each point on the central axis based on the tomographic images;

calculating, with respect to each of the three-dimensional image and the three-dimensional comparison image, a third characteristic amount representing regularity of disposition of each vertebra at each point on the central axis based on the calculated first and second characteristic amounts; and aligning positions of the third characteristic amount calculated from the three-dimensional image and the third characteristic amount calculated from the three-dimensional comparison image along the central axis.

A program of the present invention is a medical image alignment program for aligning a three-dimensional image which represents a subject having vertebrae with a three-dimensional comparison image which represents the subject and is compared with the three-dimensional image, the program causing a computer to function as:

a three-dimensional image obtaining means for obtaining the three-dimensional image and the three-dimensional comparison image;

an image generation means for generating, with respect to each of the three-dimensional image and the three-dimensional comparison image, a plurality of tomographic images orthogonal to a central axis of each vertebra of the subject along the central axis;

a first characteristic amount calculation means for calculating, with respect to each of the three-dimensional image and the three-dimensional comparison image, a first characteristic amount representing a profile in a direction orthogonal to the central axis at each point on the central axis based on the tomographic images;

a second characteristic amount calculation means for calculating, with respect to each of the three-dimensional image and the three-dimensional comparison image, a second characteristic amount representing a profile in a direction of the central axis at each point on the central axis based on the tomographic images;

a third characteristic amount calculation means for calculating, with respect to each of the three-dimensional image and the three-dimensional comparison image, a third characteristic amount representing regularity of disposition of each vertebra at each point on the central axis based on the calculated first and second characteristic amounts; and a vertebra alignment means for aligning positions of the third characteristic amount calculated from the three-dimensional image and the third characteristic amount calculated from the three-dimensional comparison image along the central axis.

The three-dimensional image and the three-dimensional comparison image may be any type of three-dimensional image as long as the first, second, and third characteristic amounts of the present invention can be calculated and a three-dimensional image obtained by CT imaging is preferably used. The three-dimensional image and the three-dimensional comparison image may be, for example, a current three-dimensional medical image of a patent and a past three-dimensional medical image of the patient for confirming progress of a disease or the like respectively.

Here, the third characteristic amount of each of the three-dimensional image and the three-dimensional comparison image representing the same patient shows a similar characteristic on the central axis, as it is less likely that the shape of vertebra does not change largely with respiration or time. Consequently, the vertebra alignment unit of the present invention may perform the alignment by matching the third characteristic amount calculated from the three-dimensional image with the third characteristic amount calculated from three-dimensional comparison image.

The first characteristic amount represents a profile in a direction orthogonal to the central axis, and quantitatively indicates a characteristic of cylindrical pattern arising from cortical bone of each vertebra along the central axis of vertebra.

A spine is formed of cervical, thoracic, lumbar, sacrum, and coccyx vertebrae and the cervical, thoracic, and lumbar vertebrae have characteristics that they have a cylindrical outer shape, with surface portions being formed of cortical bone and interior portions being formed of spongy bone, both ends of the cylindrical shape of each vertebral body are substantially planar, and a vertebral disc is located between vertebral bodies.

Consequently, due to the fact that the surface cortical bone of the vertebrae has a cylindrical shape, a high pixel value (CT value) area appears on the cylindrical shape in a trunk of vertebral bodies excluding both ends of the cylindrical shape. The first characteristic amount may be anything as long as it quantitatively represents the cylindrical pattern.

For example, the cylindrical pattern may be viewed as an annular pattern appearing on a tomographic image orthogonal to the vertebra center line and the annular pattern may be quantified as a characteristic amount orthogonal to a vector connecting the center lines and used as the first characteristic amount.

The second characteristic amount represents a profile in a direction of the central axis, and may be anything as long as it quantitatively represents a characteristic of disc shaped pattern that appears along the central axis.

Due to the fact that each vertebra has a cylindrical shape with disc shaped ends and a vertebral disc is located between vertebral bodies, a low pixel value (CT value) area representing the vertebral disc appears between the vertebral bodies. The reason why the pattern appears as a low pixel value area is that the vertebral disc has a low pixel value in comparison with the vertebral body. The second characteristic amount may be anything as long as it quantitatively represents the disc shaped pattern.

For example, a disc shaped pattern appearing adjacent to each vertebra center line in each tomographic image orthogonal to the vertebra center line along each vertebra center line may be quantified as a characteristic amount of a cross-section orthogonal to Z axis and used as the second characteristic amount.

The third characteristic amount is calculated with respect to each point on the central axis based on the first and second characteristic amounts. Here, the term "based on the first and second characteristic amounts" may include, for example, the use of eigenvalue analysis of Hessian matrix and, for example, a weighted sum of the first and second characteristic amounts may be used as the third characteristic amount.

The vertebra alignment unit may be a unit that aligns the third characteristic amount calculated from the three-dimensional image with the third characteristic amount calculated from the three-dimensional comparison image by minimizing a squared sum of the difference between the third characteristic amount calculated from the three-dimensional image and the third characteristic amount calculated from the three-dimensional comparison image using an SSD (sum of squared difference) method, or a unit that aligns the third characteristic amount calculated from the three-dimensional image with the third characteristic amount calculated from the three-dimensional comparison image by minimizing a squared sum of the difference with respect to each point on the central axis using a dynamic programming method.

Preferably, the medical image alignment apparatus of the present invention further includes an image display control unit for causing a tomographic image generated by the image generation unit to be displayed on a display device, and the image generation unit generates, from the three-dimensional image and the three-dimensional comparison image, tomographic images at corresponding positions. Here, it is preferable that the tomographic images at corresponding positions are orthogonal to central axes extracted from the three-dimensional image and the three-dimensional comparison image respectively. Further, it is preferable that the image generation unit generates a plurality of pairs of tomographic images at corresponding positions along the central axis.

The present invention provides a cross-sectional spine image display apparatus. The apparatus includes a cross-sectional image generation means for generating, by referring to a three-dimensional image data storage unit storing three-dimensional image data which includes a vertebra portion and a center line storage unit storing information of a center line that conforms to a shape of each vertebra, a plurality of cross-sectional images of the vertebrae sliced, with a plurality of positions on the center line as slice positions, by planes orthogonal to the center line passing the slice positions based on the three-dimensional image data;

a cross-sectional image display means for displaying the plurality of cross-sectional images generated at the plurality of positions side by side; and a slice position shifting means for shifting the slice positions of the plurality of cross-sectional images generated by the cross-sectional image generation means along the center line.

The slice position shifting means may be a means that shifts the slice positions of the plurality of cross-sectional images in synchronization with each other along the center line.

The slice position shifting means may be a means that sets a coordinate along the center line between adjacent vertebral discs by referring to a vertebral disc position storage unit storing position information of vertebral discs and shifts the slice positions according to the coordinate.

The slice position shifting means may be a means that sets the coordinate according to a distance between the adjacent vertebral discs on the center line.

The slice position shifting means may be a means that divides the distance between the adjacent vertebral discs on the center line at equal intervals by a predetermined number and sets each position on the divided center line as a coordinate position that can be a slice position.

The slice position shifting means may be a means that sets a position of each vertebral disc as 0% position and a position of an adjacent vertebral disc as 100% position and shifts the slice position between the 0% position and 100% position with respect to each of the plurality of cross-sections.

The slice position shifting means may be a means that gives a position between adjacent vertebral bodies to the cross-sectional image generation means as an initial slice position.

The cross-sectional image display means may be a means that identifies a position where a vertebral body size is not greater than a predetermined reference value and highlights a cross-sectional image corresponding to the identified position.

In this case, the cross-sectional image display means may be a means that determines whether or not the vertebral body size is not greater than the reference value by making cross-comparison between sizes of adjacent vertebral bodies.

Further, the present invention provides a cross-sectional spine image display method, including the steps of:

generating, by referring to a three-dimensional image data storage unit storing three-dimensional image data which includes a vertebra portion and a center line storage unit storing information of a center line that conforms to a shape of each vertebra, a plurality of cross-sectional images of the vertebrae sliced, with a plurality of positions on the center line as slice positions, by planes orthogonal to the center line passing the slice positions based on the three-dimensional image data;

displaying the plurality of cross-sectional images generated at the plurality of positions side by side; and shifting the slice positions of the plurality of cross-sectional images generated by the cross-sectional image generation means along the center line.

Still further, the present invention provides a program for causing a computer to perform the steps of:

generating, by referring to a three-dimensional image data storage unit storing three-dimensional image data which includes a vertebra portion and a center line storage unit storing information of a center line that conforms to a shape of each vertebra, a plurality of cross-sectional images of the vertebrae sliced, with a plurality of positions on the center line as slice positions, by planes orthogonal to the center line passing the slice positions based on the three-dimensional image data;

displaying the plurality of cross-sectional images generated at the plurality of positions side by side; and shifting the slice positions of the plurality of cross-sectional images generated by the cross-sectional image generation means along the center line.

According to the medical image alignment apparatus, method and program of the present invention, a plurality of tomographic images orthogonal to a central axis of each vertebra of a subject is generated along the central axis with respect to each of a three-dimensional image and a three-dimensional comparison image, a first characteristic amount representing a profile in a direction orthogonal to the central axis is calculated at each point on the central axis based on the tomographic images, a second characteristic amount representing a profile in a direction of the central axis is calculated at each point on the central axis based on the tomographic images, a third characteristic amount representing regularity of disposition of each vertebra is calculated at each point on the central axis based on the calculated first and second characteristic amounts, and positions of the third characteristic amount calculated from the three-dimensional image and the third characteristic amount calculated from the three-dimensional comparison image are aligned along the central axis. This allows accurate alignment of three-dimensional medical images of even a subject whose spine is deformed as a whole or locally by calculating third characteristic amounts representing regularity of disposition of each vertebra through quantitative density analysis based on cross-sectional shapes of two different directions of each vertebra having little deformation, and positional alignment is performed based on the third characteristic amounts. This is especially advantageous in the case where the spine is deformed by scoliosis or the like.

In the case where the first characteristic amount represents an annular pattern centered on each point on the central axis, a cross-sectional shape (annular pattern) of each vertebra having a cylindrical cortical bone orthogonal to a direction of the central axis may be quantified appropriately.

In the case where the second characteristic amount represents a disk shaped pattern orthogonal to the central axis, the disk shaped pattern arising from a vertebral disc located between each vertebral body may be quantified appropriately.

In the case where the vertebra alignment unit aligns the third characteristic amount calculated from the three-dimensional image with the third characteristic amount calculated from three-dimensional comparison image using an SSD method, a position on the central axis of the three-dimensional comparison image where the third characteristic amount of the three-dimensional image best matches with the third characteristic amount of the three-dimensional comparison image over the entire evaluation range may be accurately calculated as the position on the central axis of the three-dimensional comparison image corresponding to a given position on the central axis of the three-dimensional image.

In the case where the vertebra alignment unit aligns the third characteristic amount calculated from the three-dimensional image with the third characteristic amount calculated from three-dimensional comparison image with respect to each point on the central axis using a dynamic programming method (DP method), each position on the central axis of the three-dimensional comparison image where the third characteristic amount of the three-dimensional image best matches with the third characteristic amount of the three-dimensional comparison image may be calculated with respect to each position on the central axis of the three-dimensional image, each position on the central axis of the three-dimensional comparison image may be calculated accurately with respect to each position on the central axis of the three-dimensional image.

Further, in the case where the medical image alignment apparatus further includes an image display control unit for causing a tomographic image generated by the image generation unit to be displayed on a display device, and the image generation unit generates tomographic images at corresponding positions from the three-dimensional image and the three-dimensional comparison image, comparative image reading may be performed using images accurately aligned with each other, thus contributing to accurate image reading.

Further, in the case where the tomographic images at corresponding positions are those orthogonal to the central axis extracted from the three-dimensional image and three-dimensional comparison image respectively, comparative image reading may be performed using accurately aligned images orthogonal to the vertebra central axis, which is particularly advantageous for comparative image reading of a vertebra problem.

Still further, in the case where the image generation unit generates a plurality of pairs of tomographic images at corresponding positions along the central axis, a plurality of pairs of tomographic images at corresponding positions may be displayed comparably along the central axis, so that it is easy to understand the position on the spine of displayed tomographic images and sequentially perform comparative image reading for tomographic images of vertebrae along the vertebra center line, whereby image reading efficiency may be improved.

In the tomographic image display apparatus, method, and program of the present invention, slice positions of a plurality of cross-sectional images are shifted along the vertebra center line. Then, a plurality of cross-sectional images is generated at the shifted slice positions, and the generated images are displayed side by side, thereby allowing the user to examine a cross-sectional image of vertebra at any position on the vertebra center line. In the case where a configuration is adopted, in particular, in which slice positions of a plurality of cross-sectional image is shifted in synchronization with each other, slice positions of a plurality of cross-sectional images displayed side by side may be shifted simultaneously.

BRIEF DESCRIPTION OF THE DRAWINGS

FIG. 3A is a flowchart illustrating an operation of the medical image alignment apparatus.

FIG. 3B is a flowchart illustrating a flow of characteristic amount calculation processing of the medical image alignment apparatus.

FIG. 7 illustrates profiles of third characteristic amounts of a three-dimensional image and a three-dimensional comparison image.

FIG. 8 illustrates corresponding positions on vertebra center lines of a three-dimensional image and a three-dimensional comparison image of a first embodiment.

FIG. 16 illustrates positions of detected vertebral discs.

FIG. 17 illustrates an example coordinate setting.

DESCRIPTION OF THE PREFERRED EMBODIMENTS

Hereinafter, preferable embodiments of medical image alignment method of the present invention will be described in relation to a medical image alignment apparatus that performs the method will be described with reference to the accompanying drawings.

Figure 1:
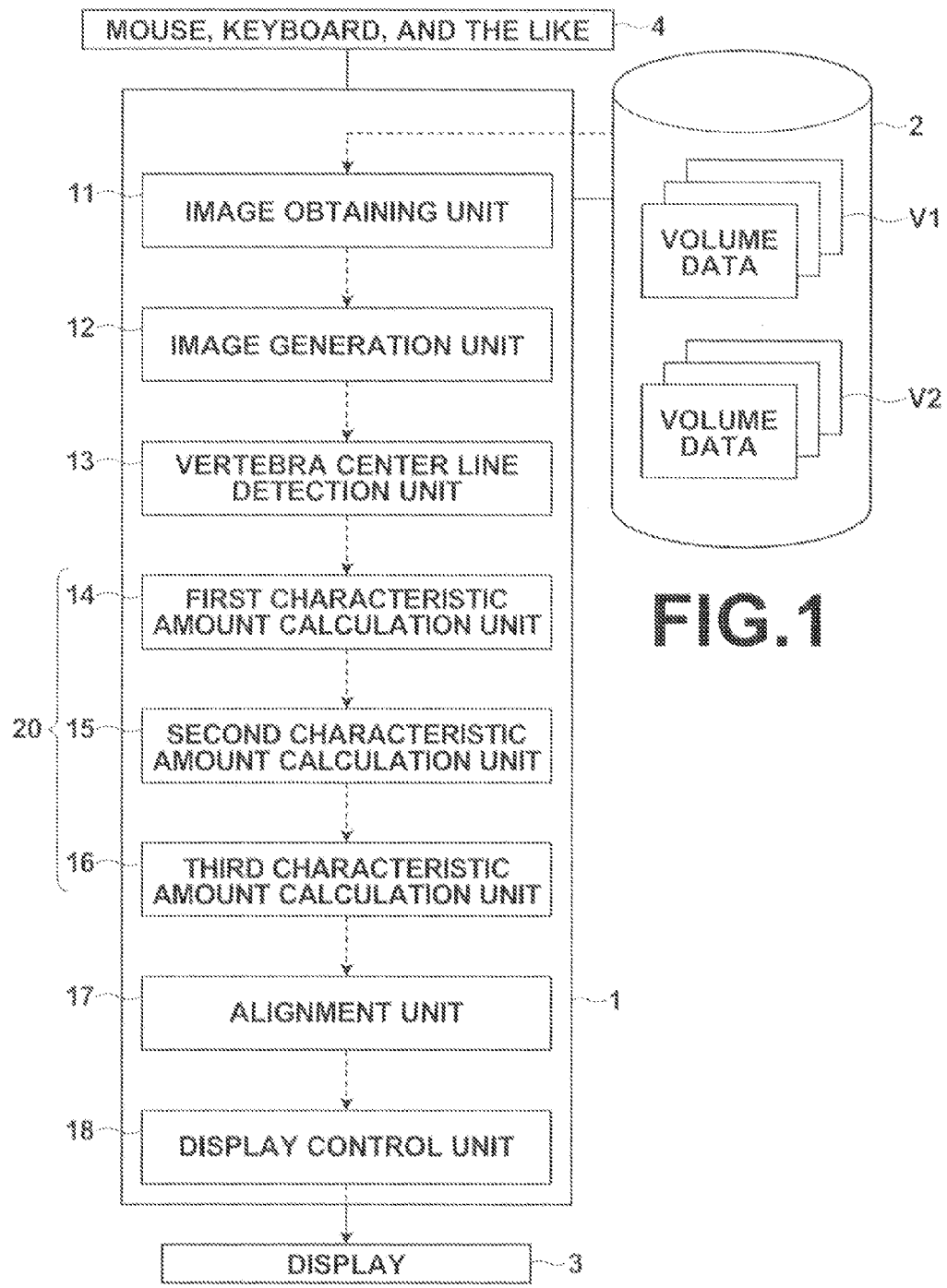
FIG. 1 is a functional block diagram of a medical image alignment apparatus according to an embodiment of the present invention.

FIG. 1 is a schematic electrical block diagram of medical image alignment apparatus 1 of the present embodiment. Medical image alignment apparatus 1 includes a processor and a memory (not shown) as a typical workstation configuration, and further includes storage 2 such as, HDD (hard disc drive) or SSD (solid state drive). Further, display 3 and input device 4, such as a mouse or keyboard, are connected to image display apparatus 1.

A medical image alignment program and data (conversion table to be described later, and the like) to be referenced by the medical image alignment program are stored in storage 2 at the time of installation and loaded in the memory at the time of startup. The medical image alignment program defines, as the processing to be performed by the CPU, image obtaining processing, image generation processing, vertebra center line detection processing, first characteristic amount calculation processing, second characteristic amount calculation processing, third characteristic amount calculation processing, alignment processing, and display control processing.

When each of the processing described above is performed by the CPU according to the prescription of the program, the general purpose workstation functions as the following units. Namely, three-dimensional image obtaining unit 11 for obtaining a three-dimensional image and a three-dimensional comparison image, image generation unit 12 for generating, with respect to each of the three-dimensional image and the three-dimensional comparison image, a plurality of tomographic images orthogonal to a central axis of each vertebra along the central axis, vertebra center line detection unit 13 for detecting center lines of vertebrae from a plurality of tomographic images, first characteristic amount calculation unit 14 for calculating, with respect to each of the three-dimensional image and the three-dimensional comparison image, a first characteristic amount representing a profile in a direction orthogonal to the central axis at each point on the central axis based on the tomographic images, second characteristic amount calculation unit 15 for calculating, with respect to each of the three-dimensional image and the three-dimensional comparison image, a second characteristic amount representing a profile in a direction of the central axis at each point on the central axis based on the tomographic images, third characteristic amount calculation unit 16 for calculating, with respect to each of the three-dimensional image and the three-dimensional comparison image, a third characteristic amount representing regularity of disposition of each vertebra at each point on the central axis based on the calculated first and second characteristic amounts, vertebra alignment unit 17 for aligning the positions of the third characteristic amount calculated from the three-dimensional image with the position of the third characteristic amount calculated from the three-dimensional comparison image along the central axes, and image display control unit 18 for causing the tomographic images generated by image generation unit 12 to be displayed on a display device.

Storage 2 includes a three-dimensional image transferred from an inspection department in charge of radiography service or obtained through database search. The three-dimensional image may be an image directly outputted from a multi-detector row computed tomography or an image generated by reconstructing a group of two-dimensional slice data outputted from a conventional CT or the like.

When detecting a selection of the alignment function of the present embodiment in a selection menu, medical image alignment apparatus 1 prompts the user to select or input information required to identify the three-dimensional image. When a current three-dimensional image V1 of a diagnosis target patient and a three-dimensional comparison image V2, which is a past three-dimensional image of the same patient, are identified through user operation, the identified three-dimensional images V1, V2 are loaded in the memory from storage 2.

Here, it is assumed that radiographing was performed with multi-detector row computed tomography in the examination of a patient and the three-dimensional images V1, V2 which include vertebrae of the patient were obtained and stored in a not shown database. Each of the three-dimensional images V1, V2 includes all of the vertebrae from cervical, through thoracic, lumbar, and sacrum to coccyx vertebrae as the vertebrae of the patient. When the alignment function is selected, and an identifier of the patient and the date of examination are inputted by the user, a relevant three-dimensional image V1 and a three-dimensional comparison image V2 are obtained and stored in storage 2, whereby the image display method of the present invention is performed.

Image obtaining unit 11 obtains the three-dimensional image V1 and the three-dimensional comparison image V2, each including vertebral bodies. Image obtaining unit 11 may obtain, as the three-dimensional image V1 and the three-dimensional comparison image V2, not only medical images, such as CT images, MRI images, RI images, PET images, or X-ray images, but also artificial two-dimensional or three-dimensional medical images, such as generated three-dimensional images or artificially created three-dimensional medical images, or the like.

Image generation unit 12 generates, with respect to each of the three-dimensional image V1 and the three-dimensional comparison image V2, each including vertebral bodies, obtained by image obtaining unit 11, a plurality of first tomographic images (e.g., axial tomographic images) along a predetermined axis direction (e.g., body axis direction). Image generation unit 12 stores the generated plurality of first tomographic images in the memory. When a plurality of first tomographic images, which is axial cross-sections of a three-dimensional medical image having vertebral bodies is directly obtained by image obtaining unit 11, image generation unit 12 obtained the plurality of first tomographic images as they are and stores them in the memory.

Further, image generation unit 12 generates, with respect to each of the three-dimensional image V1 and the three-dimensional comparison image V2 obtained by image obtaining unit 11, a plurality of tomographic images (second tomographic images) orthogonal to central axes $Z_1'$, $Z_2'$ of vertebrae in the three-dimensional image V1 and the three-dimensional comparison image V2 respectively along the central axes $Z_1'$, $Z_2'$ of vertebrae, to be described later. In addition, image generation unit 12 may change the range of the spatial region of an image to be generated as appropriate. Further, image generation unit 12 according to the present embodiment generates tomographic images at corresponding positions of the three-dimensional image V1 and the three-dimensional comparison image V2 aligned by alignment unit 17, as will be described later. Further, a plurality of such pairs of tomographic images at corresponding positions of the three-dimensional image V1 and the three-dimensional comparison image V2 is generated along the central axes $Z_1'$, $Z_2'$ of the three-dimensional image V1 and the three-dimensional comparison image V2. Note that an X' Y' Z' coordinate system set with the center line A of vertebrae as the Z' axis is sometimes denoted herein as an $X_1'Y_1'Z_1'$ coordinate system for the three-dimensional image V1 and as an $X_2'Y_2'Z_2'$ coordinate system for the three-dimensional comparison image V2. Further, a position (X', Y', Z') of the X'Y' Z' coordinate system set with the center line A of vertebrae as the Z' axis is sometimes denoted as $(X_1', Y_1', Z_1')$ for the three-dimensional image V1 and as $(X_2', Y_2', Z_2')$ for the three-dimensional comparison image V2.

Vertebra center line detection unit 13 detects a center line of each vertebra included in each of the plurality of first tomographic images generated by image generation unit 12.

Figure 2:
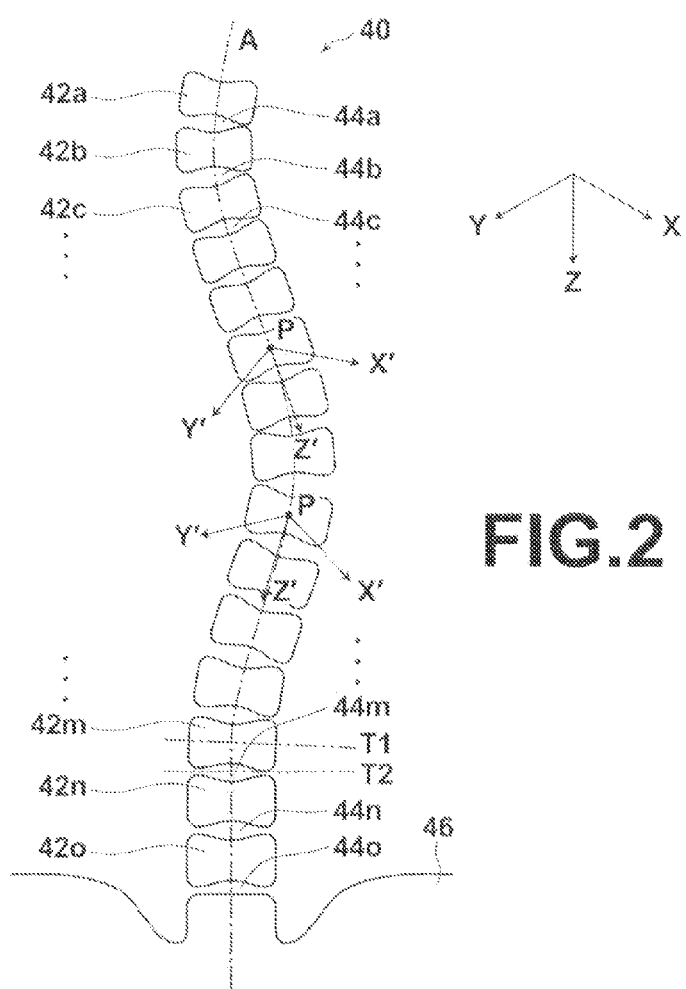
FIG. 2 is a schematic view of vertebral bodies, illustrating that a center line of each vertebra is detected by a vertebra center line detection unit.

FIG. 2 is a schematic view of a sagittal image representing the disposition of each vertebra. Vertebral body group 40 includes 15 vertebrae 42, each having a substantially cylindrical cortical bone. Each vertebra 42 is disposed in an S-shaped curve with respect to the body axis (Z axis). That is, each vertebra 42 can be said to be disposed along the center line A of the S-curve (hereinafter, the coordinate axis along the center line A is referred to as "Z axis").

Further, a vertebral disc 44 is located between adjacent vertebrae 42. For the sake of simplicity, vertebral discs 44 are not drawn in FIG. 2 and illustrated, instead, as a gap between vertebrae 42.

Further, in order to distinguish each of vertebrae 42 and vertebral discs 44, an alphabet is suffixed to the reference numerals 42, 44. That is, the vertebrae and vertebral discs are denoted as vertebrae 42a to 42o and as vertebral discs 44a to 44o from the top. Note that the lower side of the bottom vertical disc 44o and pelvis 46 are joined.

In order to directly detect a center line A of each vertebra using a plurality of first tomographic images, a very sophisticated image processing technology is required. Consequently, various detection methods focusing attention on structural characteristics of vertebral bodies may be used. For example, a center line of a not shown spinal marrow, which can be detected relatively easily by image processing, may be obtained in advance and the center line A of each vertebra 42 may be detected accurately based on the relative positional relationship between the spinal marrow and each vertebra 42 (for further details, refer to Japanese Unexamined Patent Publication No. 2009-207727).

As for the detection method of the spinal marrow, template matching, demarcation method, or learning method based on Adaboost for generating an integrated learned machine may be used.

First characteristic amount calculation unit 14, second characteristic amount calculation unit 15, and third characteristic amount calculation unit 16 constituting characteristic amount calculation unit 20 will now be described.

First characteristic amount calculation unit 14 calculates, with respect to each of the three-dimensional image V1 and the three-dimensional comparison image V2, a first characteristic amount representing a profile in a direction orthogonal to the central axis of vertebrae 42 (FIG. 2) at each point on the central axis based on a plurality of second tomographic images. As the first characteristic amount, for example, a characteristic amount that extracts an annular pattern centered on a given point P on the Z' axis is used. For the calculation of this characteristic amount, eigenvalue analysis of Hessian matrix, to be described later, is used. First characteristic amount calculation unit 14 stores the calculated first characteristic amount in the memory.

Second characteristic amount calculation unit 15 calculates, with respect to each of the three-dimensional image V1 and the three-dimensional comparison image V2, a second characteristic amount representing a profile in a direction of the central axis of vertebrae 42 (FIG. 2) at each point on the central axis based on a plurality of second tomographic images. As for the second characteristic amount, for example, a characteristic amount that extracts an tubular pattern extending in a Z' axis direction centered on a given point on the Z' axis is used. For the calculation of this characteristic amount, eigenvalue analysis of Hessian matrix, to be described later, is used. Second characteristic amount calculation unit 15 stores the calculated second characteristic amount in the memory.

Third characteristic amount calculation unit 16 calculates, with respect to each of the three-dimensional image V1 and the three-dimensional comparison image V2, a third characteristic amount representing regularity of disposition of each vertebra 42 at each point on the central axis based on the calculated first and second characteristic amounts. As for the third characteristic amount, for example, a weighted sum of the first and second characteristic amounts is used. Third characteristic amount calculation unit 16 stores the calculated third characteristic amount in the memory.

Alignment unit 17 aligns the positions of the third characteristic amount calculated from the three-dimensional image V1 and third characteristic amount calculated from three-dimensional comparison image V2 along the central axis.

FIG. 7 illustrates an example graph 31 that shows a profile of the third characteristic amount of the three-dimensional image V1 and an example graph 32 that shows a profile of the third characteristic amount of the three-dimensional comparison image V2. The third characteristic amount represents a periodicity of vertebrae, and the third characteristic amount of each of the three-dimensional image V1 and the three-dimensional comparison image V2 representing the same patient shows a similar characteristic on the central axis Z', as it is less likely that the shape of vertebra does not change largely with respiration or time. That is, each characteristic amount is analogous to each other along the central axis, as shown in FIG. 7. In the present embodiment, the third characteristic amount of the three-dimensional image V1 is matched with the third characteristic amount of the three-dimensional comparison image V2, and corresponding positions of the third characteristic amount of the three-dimensional image V1 and the third characteristic amount of the three-dimensional comparison image V2 on the central axis Z' are calculated in the following manner. Note that, as pre-processing for matching the third characteristic amount of the three-dimensional image V1 with the third characteristic amount of the three-dimensional comparison image V2 shown in FIG. 7, processing, such as scale size adjustment in the Z' axis direction and the like, may be performed on the third characteristic amount of the three-dimensional image V1 and the third characteristic amount of the three-dimensional comparison image V2.

Alignment unit 17 determines, by an SSD method, a shift amount of a position on the central axis Z' (A2) of the three-dimensional comparison image V2 with respect to a position on the central axis Z' (A1) of the three-dimensional image V1 where the third characteristic amount calculated from the three-dimensional image V1 best matches with the third characteristic amount calculated from the three-dimensional comparison image V2. Then, alignment unit 17 determines corresponding positions of the three-dimensional image V1 and the three-dimensional comparison image V2 on the central axes Z' from the determined shift amount s and converts the corresponding positions to positions in XYZ coordinates. Alignment unit 17 stores the corresponding positions of the three-dimensional image V1 and the three-dimensional comparison image V2 on the central axes Z' and converted positions in XYZ coordinates in the memory.

Display control unit 18 causes tomographic images generated by image generation unit 12 to be displayed on a display device. Further, display control unit 18 causes display 3 to display tomographic images at corresponding positions of the three-dimensional image V1 and the three-dimensional comparison image V2 aligned by alignment unit 17. In the present embodiment, image generation unit 12 generates the tomographic images at the corresponding positions from the three-dimensional image V1 and the three-dimensional comparison image V2. Further, a plurality of such pairs of tomographic images at corresponding positions is generated from the three-dimensional image V1 and the three-dimensional comparison image V2 along the central axes $Z_1'$, $Z_2'$ of the three-dimensional image V1 and the three-dimensional comparison image V2. Display control unit 18 causes a pair of tomographic images at corresponding positions generated by image generation unit 12 to be comparably displayed. Note that the tomographic images at corresponding positions may be tomographic images orthogonal to the central axes $Z_1'$, $Z_2'$ determined from the three-dimensional image V1 and the three-dimensional comparison image V2. The term "comparably displayed" as used herein refers to that the tomographic image pair is displayed in any form as long as it allows the user, such as a doctor, to compare them, but it is preferable that the tomographic image pair is displayed side by side in the same size, and tomographic images in the pair may be displayed in a switched manner.

FIGS. 3A, 3B are flowcharts illustrating a flow of medical image alignment processing. An operation of medical image alignment apparatus 1 will be described according to the flowcharts of FIGS. 3A, 3B.

First, image obtaining unit 11 obtains a three-dimensional medical image V1 and the three-dimensional medical comparison image V2 both of which include vertebral bodies. (S01).

Then, image generation unit 12 generates a plurality of X-Y cross-sectional images along the body axis (Z axis) direction, i.e., a plurality of first tomographic images based on the three-dimensional medical image V1, including vertebral bodies, obtained by image obtaining unit 11 (S02A).

When a plurality of first tomographic images, which is axial cross-sections of the three-dimensional medical image V1, is obtained by image obtaining unit 11, image generation unit 12 obtained the plurality of first tomographic images.

Then, from the plurality of first tomographic images of the three-dimensional image V1 obtained in step S01, vertebra center line detection unit 13 detects a center line A1 of vertebra 42 included in each of the images (S03A). Using the detection method described above, vertebra center line detection unit 13 detects the center line A of vertebrae 42 shown in FIG. 2 from the plurality of first tomographic images of the three-dimensional image V1. (The center line A extracted from the plurality of first tomographic images of the three-dimensional image V1 is, hereinafter, referred to as "center line A1".) Thereafter, the center line A1 is set as a new coordinate axis ($Z_1'$ axis) of the three-dimensional image V1. Note that an X'Y'Z' coordinate system set with the center line A of vertebrae as the Z' axis is sometimes denoted herein as an $X_1'Y_1'Z_1'$ coordinate system for the three-dimensional image V1 and as an $X_2'Y_2'Z_2'$ coordinate system for the three-dimensional comparison image V2. Further, a position (X', Y', Z') of the X'Y'Z' coordinate system set with the center line A of vertebrae as the Z' axis is sometimes denoted as ($X_1'$, $Y_1'$, $Z_1'$) for the three-dimensional image V1 and as ($X_2'$, $Y_2'$, $Z_2'$) for the three-dimensional comparison image V2.

Then, image generation unit 12 generates a plurality of $X_1'$-$Y_1'$ cross-sectional images along the center line A1 ($Z_1'$ axis) detected in step S03A, i.e., a plurality of second tomographic images based on the three-dimensional medical image V1 obtained in step S01 (S04A). Instead of using all image information of the obtained three-dimensional medical image, image generation unit 12 may generate a plurality of second tomographic images using only image information which can be reconstructed in a portion of images adjacent to the Z' axis covering the area of vertebral body group 40. This may reduce the memory space used and calculation time by control unit 14.

Next, characteristic amount calculation unit 20 calculates first to third characteristic amounts at each point on Z1' axis from the plurality of second tomographic images obtained in step S04A (S05A). The calculation method for the characteristic amounts will be described later.

In the mean time, image generation unit 12 generates a plurality of X-Y cross-sectional images along the body axis (Z axis) direction, i.e., a plurality of first tomographic images based on the three-dimensional comparison medical image V2, including vertebral bodies, obtained by image obtaining unit 11 (S02B). When a plurality of first tomographic images, which is axial cross-sections of the three-dimensional comparison image V2, is obtained by image obtaining unit 11, image generation unit 12 obtains the plurality of second tomographic images obtained by image obtaining unit 11.

Then from the plurality of second tomographic images of the three-dimensional comparison image V2 obtained in step S01, vertebra center line detection unit 13 detects a center line A2 of vertebra 42, as shown in FIG. 2, included in each of the images as in the manner described above (S03B). (The center line A extracted from the plurality of first tomographic images of the three-dimensional comparison image V2 is, hereinafter, referred to as "center line A2".) Thereafter, the center line A2 is set as a new coordinate axis ($Z_2'$ axis) of the three-dimensional comparison image V2.

Then, image generation unit 12 generates a plurality of $X_2'$-$Y_2'$ cross-sectional images along the center line A2 ($Z_2'$ axis) detected in step S03B, i.e., a plurality of second tomographic images based on the three-dimensional medical image V1 obtained in step S01 (S04B).

Then, characteristic amount calculation unit 20 calculates first to third characteristic amounts at each point on $Z_2'$ axis from the plurality of second tomographic images obtained in step S04B (S05B).

Here, the calculation processing for calculating the first to third characteristic amounts performed by characteristic amount calculation unit 20 in steps S05A and S05B respectively will now be described in detail by breaking step S05A or S05B into steps S21 to S23.

First characteristic calculation unit 14 calculates the first characteristic amount (S21). The first characteristic amount can be represented by formula (1) given below.

A spine is formed of cervical, thoracic, lumbar, sacrum, and coccyx vertebrae and the cervical, thoracic, and lumbar vertebrae have characteristics that they have a cylindrical outer shape, with surface portions being formed of cortical bone and interior portions being formed of spongy bone, both ends of the cylindrical shape of each vertebral body are substantially planar, and a vertebral disc is located between vertebral bodies.

Consequently, due to the fact that the surface cortical bone of the vertebrae has a cylindrical shape, a high pixel value (CT value) area appears on the cylindrical shape in a trunk of vertebral bodies excluding both ends of the cylindrical shape. The first characteristic amount may be anything as long as it quantitatively represents the cylindrical pattern. In the present embodiment, the cylindrical pattern is viewed as an annular pattern appearing on a tomographic image orthogonal to the vertebra center line and, as a characteristic amount orthogonal to a vector connecting the vertebra center lines, quantified by formula (1) given below and used as the first characteristic amount.

$$f_1(z') = \int\int_{(x',y',z') \in R} \frac{\lambda_1(x', y', z')}{|\lambda_2(x', y', z')| + |\lambda_3(x', y', z')| + \varepsilon} \left| \vec{E_1}(x', y', z') \cdot \vec{d} \right| dx'dy' \quad (1)$$

where, (x', y', z') indicates a position in the X', Y', Z' coordinate system. The integration region R represents points in a second tomographic image and represents a cortical bone region of vertebra 42.

Eigenvalues and eigenvectors in a 3×3 Hessian matrix are $(\lambda_1, \lambda_2, \lambda_3)$ and $(E_1, E_2, E_3)$ respectively. $\lambda_1 \leq \lambda_2 \leq \lambda_3$. Vector "d" is a vector from a point (0, 0, Z') on the Z' axis toward (x', y', z') and d=(x', y', 0). The $\varepsilon$ is a small positive integer for preventing division by zero.

Figure 4A:
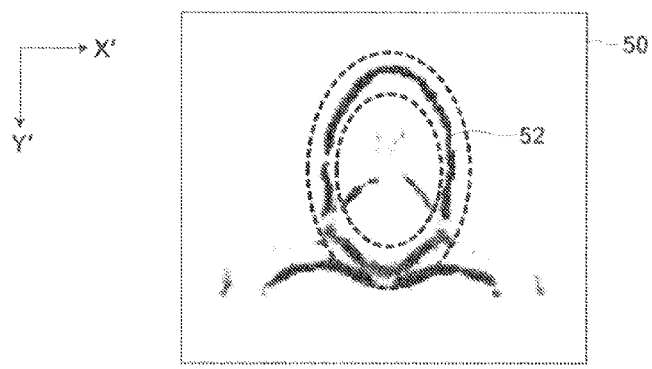
FIG. 4A is a schematic view illustrating a two dimensional distribution of a first characteristic amount (integrand) at a center position of a cross-section of a vertebra.
Figure 4B:
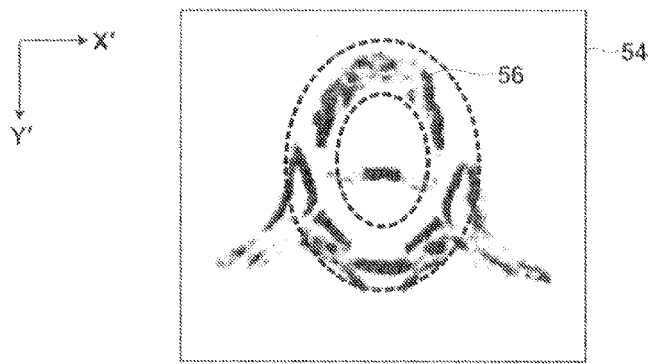
FIG. 4B is a schematic view illustrating a two dimensional distribution of a first characteristic amount (integrand) at a position of cross-section between vertebrae.

FIGS. 4A, 4B are schematic views illustrating two-dimensional distributions of first characteristic amounts (integrand) at the respective cross-sectional positions. That is, values of the first characteristic amount (integrand) in the second tomographic images are visualized as image density. The density at a position having a large first characteristic amount is thick while the density at a position having a small first characteristic amount is thin.

FIG. 4A is a schematic view of a visual image 50 representing calculated values of the first characteristic amount at the cross-sectional position T1 (FIG. 2). As the cross-sectional position T1 is the midpoint of a vertebra 42, the second tomographic image includes a cross-sectional shape of the cortical bone of the vertebra 42. Therefore, an annular black pattern 52 appears vividly in the visual image 50. Consequently, the first characteristic amount which is the sum of integrands in the integration region R becomes large. The integration region R represents a surface portion (cortical bone region) of the vertebra.

In the mean time, FIG. 4B is a schematic view of a visual image 54 representing calculated values of the first characteristic amount at the cross-sectional position T2 (FIG. 2). As the cross-sectional position T2 is the position of vertebral disc 44m, the second tomographic image does not includes the cross-sectional shape of cortical bone of the vertebra 42 and, instead, includes a peripheral portion of the vertebral disc 44. Therefore, an annular thin pattern 56 subtly appears in the visual image 54. Consequently, the first characteristic amount which is the sum of integrands in the integration region R becomes small.

As another calculation example of the first characteristic amount, for example, a Laplacian filter (second derivative filter) for detecting edge intensity may be used. Further, a Laplacian of Gaussian filter (hereinafter, the "LOG filter") which smoothes pixels in a local region by applying Gaussian weighting and filters them to find a zero crossing as an edge may be used.

Next, second characteristic amount calculation unit calculates second characteristic amounts from the plurality of second tomographic images obtained in step S04A or S04B (S22).

Due to the fact that each vertebra has a cylindrical shape with disc shaped ends and a vertebral disc is located between vertebral bodies, a low pixel value (CT value) area representing the vertebral disc appears between the vertebrae. The reason why the pattern appears as a low pixel value area is that the vertebral disc has a low pixel value in comparison with the vertebra. The second characteristic amount may be anything as long as it quantitatively represents the disc shaped pattern.

In the present embodiment, a disc shaped pattern appearing adjacent to each vertebra center line in each tomographic image orthogonal to the vertebra center line along each vertebra centerline is quantified by formula (2) given below as a characteristic amount of a cross-section orthogonal to Z axis and used as the second characteristic amount.

The second characteristic amount is represented by formula (2) given below.

$$f_2(z') = \int\int_{(x',y',z') \in c} \frac{\lambda_1(x', y', z')}{|\lambda_2(x', y', z')| + |\lambda_3(x', y', z')| + \varepsilon} \left| \vec{E_1}(x', y', z') \cdot \vec{e_z} \right| dx'dy' \quad (2)$$

where, (x', y', z') indicates a position in the X', Y', Z' coordinate system. The integration region C represents an area adjacent to the center line A (Z' axis).

As in formula (1) above, eigenvalues and eigenvectors in a 3×3 Hessian matrix are $(\lambda_1, \lambda_2, \lambda_3)$ and $(E_1, E_2, E_3)$ respectively. また $\lambda 1 \leq \lambda 2 \leq \lambda 3$ である。 $\lambda_1 \leq \lambda_2 \leq \lambda_3$. "ez" represents a unit vector (0, 0, 1) on the Z' axis. The C is a small positive integer for preventing division by zero.

Figure 5:
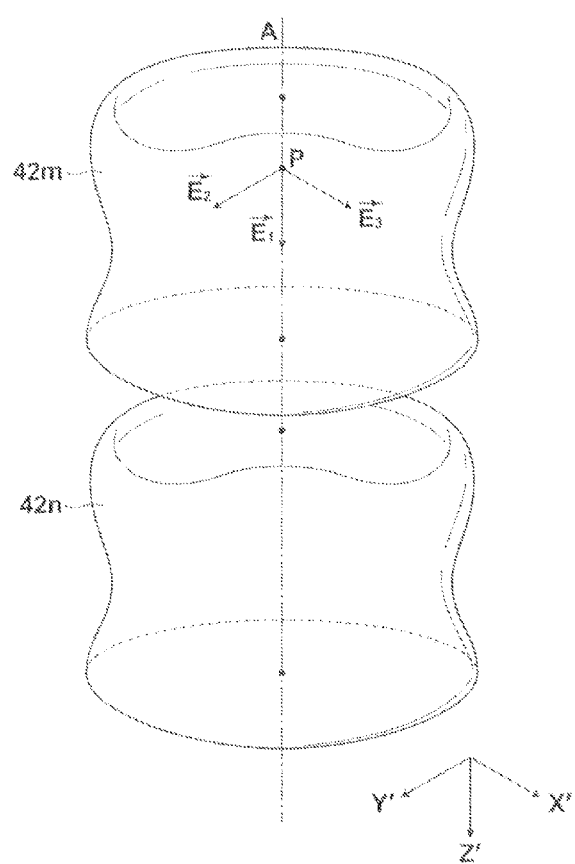
FIG. 5 is a schematic view illustrating correspondence relationship between a three-dimensional shape of a vertebral body and an eigenvector of Hessian matrix at an internal point.

FIG. 5 is a schematic view illustrating correspondence relationship between a three-dimensional shape of vertebral body 42m and eigenvectors E1 to E3 of Hessian matrix at internal point P. Eigenvector $E_1$ corresponding to minimal eigenvalue $\lambda_1$ of Hessian matrix is oriented in an extended direction of vertebra 42m (Z' direction). Therefore, as can be seen from the shape of the integrand of formula (2), the second characteristic amount extracts a planar shape without density gradient with reference to point P, in particular, only a vector component in the Z' axis direction. That is, the second characteristic amount is said to be a characteristic amount that extracts a disc shaped pattern extending in the Z' axis direction.

Then, third characteristic amount calculation unit 16 calculates a third characteristic amount based on the first characteristic amounts calculated in step S21 and second characteristic amount calculated in step S22 (step S23).

The first characteristic amount clearly represents the trunk of the cylindrical shape of a vertebral body while the second characteristic amount clearly represents a vertebral disc. Consequently, the combination the two characteristic amounts may clearly indicate the repetition period of vertebral bodies and vertebral discs. Further, the first characteristic amount and second characteristic amount have opposing signs to each other, so that the periodicity may be represented significantly by combining them.

The third characteristic amount may be represented by formula (3) given below.

$$f_3(z') = f_1(z') + \alpha \max_{\sigma \in [\sigma_0 \cdot \sigma_1]} \left[ \frac{d^2 G(z', \sigma)}{dz'^2} \otimes f_2(z') \right] \quad (3)$$

where, $\alpha$ is an arbitral weighting factor and $G(z', \sigma)$ is Gaussian function with G as standard deviation.

Figure 6A:
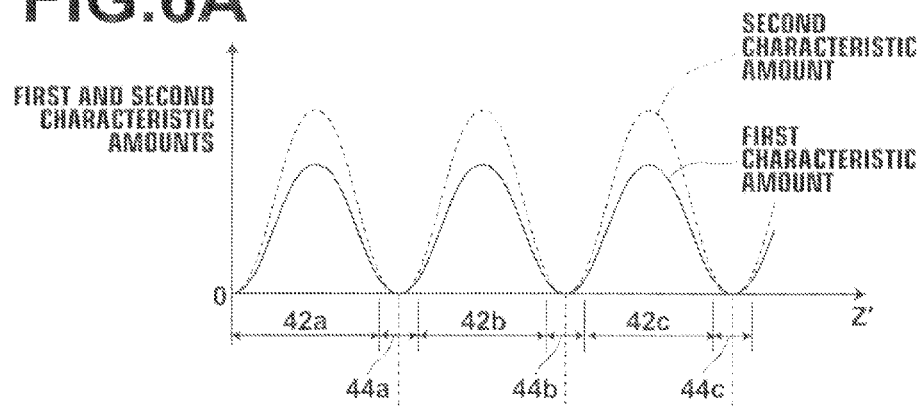
FIG. 6 illustrates profiles of characteristic amounts, in which A illustrates profiles of first and second characteristic amounts in Z' axis direction, B illustrates a profile of the second characteristic amount after subjected to LOG filtering, and C illustrates a profile of a third characteristic amount in Z' axis direction.
Figure 6B:
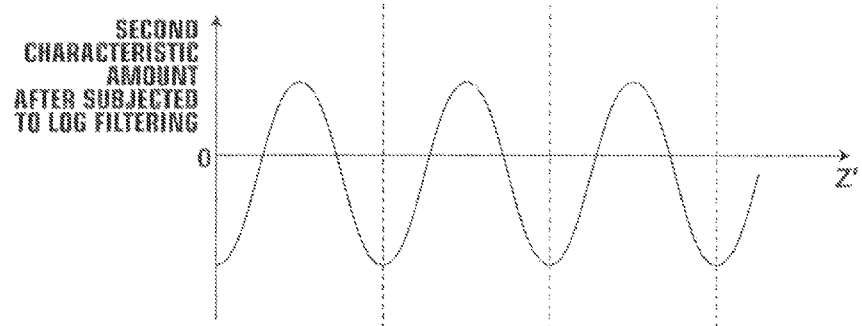
Figure 6C:
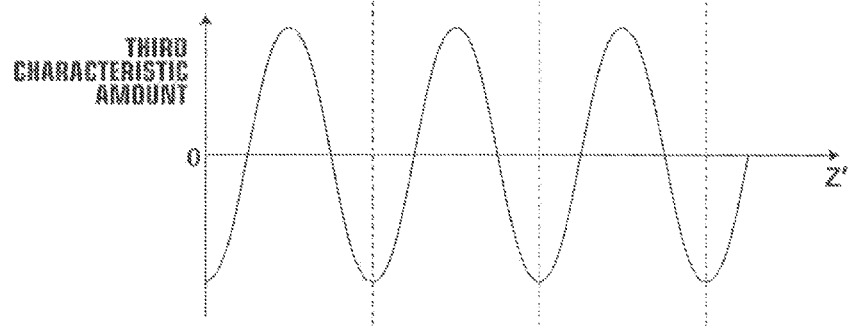

A to C of FIG. 6 illustrate profiles of first to third characteristic amounts in Z' axis direction.

A of FIG. 6 illustrates profiles of first and second characteristic amounts in Z' axis direction. The first characteristic amount (solid line) and second characteristic amount (dotted line) take local maximum values at the middle position of vertebra 42 (cross-sectional position T1 in FIG. 2) and local minimum values at the position of vertebral disc 44 (cross-sectional position T2 in FIG. 2).

B of FIG. 6 illustrates a profile of second characteristic amount after subjected to LOG filtering. As a point where the quadratic differential value is zero is extracted from the profile of second characteristic amount (A of FIG. 6), so that the profile shown in B of FIG. 6 has a shape of periodic function. The profile takes a local maximum at the middle position of vertebra 42 (cross-sectional position T1 in FIG. 2) and a local minimum value at the position of vertebral disc 44 (cross-sectional position T2 in FIG. 2).

In the mean time, the shape of the profile shown in B of FIG. 6 varies according to the value of G in the Gaussian function G (z', σ). In the present embodiment, a value of G where the value of the profile becomes maximal is selected within a predetermined range σ0 to σ1.

C of FIG. 6 illustrates the profile of third characteristic amount in Z' axis direction. The third characteristic amount represents the sum of the first characteristic amount f1 (Z') and a characteristic amount obtained by applying LOG filter to the second characteristic amount f2 (Z').

This generates a third characteristic amount f3 (Z') that represents regularity of disposition of each vertebra 42. The third characteristic amount takes a local maximum value at the middle position of vertebra 42 (cross-sectional position T1 in FIG. 2) and a local minimum value at the position of vertebral disc 44 (cross-sectional position T2 in FIG. 2).

Herein, characteristic amount calculation unit 20 performs processing of S21 to S23 on the three-dimensional medical image V1 and the three-dimensional medical comparison image V2 in steps S05A and S05B to calculate the first to third characteristic amounts and obtains third characteristic amount f31 (z'), f32 (z') shown in FIG. 7.

Then, alignment unit 17 aligns positions along the central axes $Z_1'$, $Z_2'$ of the third characteristic amount f31 (z') calculated from the three-dimensional image V1 and third characteristic amount f32 (z') calculated from the three-dimensional comparison image V2 (S06).

As described above, the third characteristic amount f31 (z') calculated from the three-dimensional image V1 and third characteristic amount f32 (z') calculated from the three-dimensional comparison image V2 are those calculated from the vertebrae of the same patient, so that it can be said that third characteristic amounts at corresponding positions of each vertebra are similar. Consequently, in the present embodiment, vertebta alignment unit 17 shifts the third characteristic amount f32 (z') calculated from the three-dimensional comparison image V2 on the Z' axis and calculates a shift amount s at a position where the third characteristic amount f31 (z') calculated from the three-dimensional image V1 best matches with the third characteristic amount f32 (z') calculated from the three-dimensional comparison image V2.

More specifically, alignment unit 17 determines, based on SSD method, that the smaller the cost function represented by formula (4) given below, the higher the correlation between the third characteristic amount f31(z') calculated from the three-dimensional image V1 and the third characteristic amount f32(z') calculated from the three-dimensional comparison image V2, calculates a shift amount s that minimizes the cost function represented by formula (4), and stores the calculated shift amount in the memory.

According to this method, a single shift amount s that best matches each third characteristic amount of the three-dimensional image V1 with three-dimensional comparison image V2 over the entire range of 0≤z'≤Z' may be obtained.

$$\min_{s} \text{arc} \sum_{z'=0}^{Z'} (f_{32}(z' + s) - f_{31}(z'))^2 \quad (4)$$

Then, alignment unit 17 determines positions on central axis Z' where the three-dimensional image V1 and the three-dimensional comparison image V2 correspond to each other from the calculated shift amount. More specifically, the position P2 (0, 0, z'+s) on the central axis $Z_2'$ of the three-dimensional comparison image V2 that minimizes the aforementioned evaluation function is calculated as the position corresponding to the position P1 (0, 0, z') on the central axis of the three-dimensional image V1, as illustrated in FIG. 7.

FIG. 8 illustrates corresponding positions on each vertebra center line of the three-dimensional image and the three-dimensional comparison image in the first embodiment. As illustrated in FIG. 8, n positions $P1_i$ (0≤i≤n, i and n are positive integers) are sequentially set at an equal interval on the central axis $Z_1'$ of the three-dimensional image V1 within the range 0≤z'≤Z' from the cervical vertebrae toward caudal vertebrae in the present embodiment. Then, with respect to each position $P1_i$ ($0 \leq i < n$) on the central axis $Z_1'$ of the three-dimensional image V1, a position $P2_i$ (0, 0, $z_i'$+s) on the central axis $Z_2'$ of the three-dimensional image V2 corresponding to position $P1_i$ (0, 0, $z_i'$) is obtained.

Then, alignment unit 17 converts corresponding positions on the central axis Z' of the three-dimensional image V1 and the three-dimensional comparison image V2 to a position in an XYX coordinate system (S08). Vertebra position estimation unit 36 converts the position of each vertebra 42 on Z' axis estimated in step S08 to a position in the XYZ coordinate system. As the positional relationship between the point P on Z' axis and the XYZ coordinate is known, such coordinate conversion is easy.

In the present embodiment, each position $P1_i$ ($0 \leq i < n$) set along the central axis $Z_1'$ of the three-dimensional image V1 at an equal interval within the range $0 \leq z' \leq Z'$ is converted to obtain a corresponding coordinate $Q1_i$ ($0 \leq i < n$), as illustrated in FIG. 8. In addition, each position $P2_i$ ($0 \leq i < n$) on central axis $Z_2'$ of the three-dimensional image V2 corresponding to each position $P1_i$ ($0 \leq i < n$) on the central axis $Z_1'$ of the three-dimensional image V1 is also converted and a corresponding XYZ coordinate $Q2_i$ ($0 \leq i < n$) is obtained.

Further, in the present embodiment, tomographic images at corresponding positions are generated based on the calculated positions in the XYZ coordinate system and displayed. In the first embodiment, with respect to calculated corresponding positions $Q1_i$ and $Q2_i$ ($0 \leq i < n$) on the central axes of the three-dimensional image V1 and the three-dimensional comparison image V2, a pair of axial tomographic image $Img1_i$, which includes $Q1_i$ of the three-dimensional image V1, and axial tomographic image $Img2_i$, which includes $Q2_i$ of the three-dimensional comparison image V2, is generated based on the positions in the XYZ coordinate system (S09).

Figure 9:
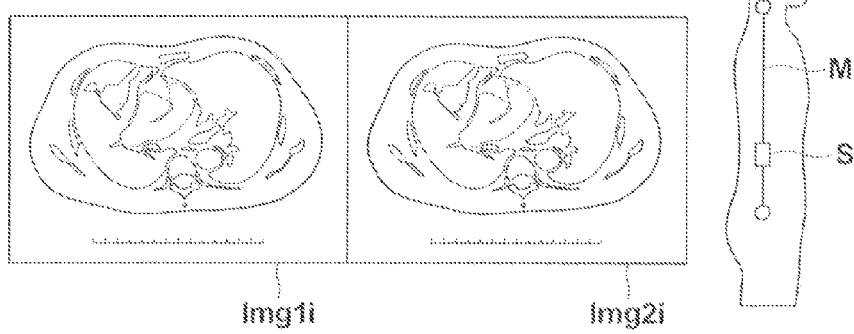
FIG. 9 illustrates an example display screen, showing tomographic images at the corresponding positions of the three-dimensional image and the three-dimensional comparison image of the first embodiment.

FIG. 9 illustrates an example image display in which axial tomographic image $Img1_i$ of three-dimensional image and axial tomographic image $Img2_i$ of three-dimensional image at corresponding positions are comparably displayed. Finally, display control unit 18 comparably displays the axial tomographic images $Img1_i$ and $Img2_i$ at corresponding positions, as illustrated in FIG. 9.

In the present embodiment, display control unit 18 is designed to receive an instruction to start comparative image reading from the user through, for example, a button provided in GUI and to comparably display axial images $Img1_0$ and $Img2_0$ at a predetermined position from among a plurality of pairs of axial tomographic images $Img1_i$ and $Img2_i$.

Further, in the present embodiment, control unit 18 displays a mark representing the vertebra center line of the tomographic images and a slider S that indicates the position on the vertebra center line of the currently displayed tomographic images on the right side of the display screen, as illustrated in FIG. 9. In the present embodiment, the slider S is movable by an input device, such as a mouse, and the user may drag and move the slider S along the mark M representing the center line and display, in series, each pair of a plurality of axial tomographic images $Img1_i$ and $Img2_i$ ($0 \leq i < n$, i and n are positive integers) along cervical vertebra center lines A1 and A2 of the three-dimensional image V1 and the three-dimensional comparison image V2 according to the position of the slider on the center line.

As described above, according to the first embodiment, with respect to each of a three-dimensional image and a three-dimensional comparison image, a plurality of tomographic images orthogonal to the central axis of each vertebra of a subject is generated along the central axis, a first characteristic amount representing a profile in a direction orthogonal to the central axis is generated at each point on the central axis based on the tomographic images, a second characteristic amount representing a profile in a direction of the central axis is generated at each point on the central axis based on the tomographic images, a third characteristic amount representing regularity of disposition of each vertebra is generated at each point on the central axis based on the calculated first and second characteristic amounts, and positions of the third characteristic amount calculated from the three-dimensional image and the third characteristic amount calculated from the three-dimensional comparison image along the central axes are aligned with each other. This allows accurate alignment of three-dimensional medical images of even a subject whose spine is deformed as a whole or locally by calculating third characteristic amounts representing regularity of disposition of each vertebra through quantitative density analysis based on cross-sectional shapes of two different directions of each vertebra having little deformation and positional alignment is performed based on the third characteristic amounts. This is especially advantageous in the case where the spine is deformed by scoliosis or the like.

Further, when positional alignment is performed based on a Z axis direction as in a conventional method, an error may occur due to respiration or a temporal change in the length of spine. But as in the present embodiment, by performing positional alignment based on a vertebra which is less likely to be influenced by respiration or posture, tomographic images of the same position may be displayed accurately. This may contribute to more accurate comparative image reading.

Further, as the first characteristic amount represents an annular pattern centered on a point on the central axis, a cross-sectional shape (i.e., annular pattern) orthogonal to a direction of the central axis of each vertebra having a substantially cylindrical cortical bone may be quantified appropriately.

Still further, as the second characteristic amount represents a pattern along the central axis, a cross-sectional shape (i.e., disc shaped pattern) parallel to a direction of the central axis of each vertebra having a substantially cylindrical cortical bone may be quantified appropriately.

Further, as vertebta alignment unit 17 aligns the positions of the third characteristic amount calculated from the three-dimensional image V1 and third characteristic amount calculated from the three-dimensional comparison image V2 using the SSD method, a position on the central axis of the three-dimensional comparison image corresponding to a given position on the central axis of the three-dimensional image, where the third characteristic amount of the three-dimensional image best matches with the third characteristic amount of the three-dimensional comparison image over the entire evaluation range, may be calculated accurately.

In the first embodiment, the apparatus further includes image display control unit 18 for causing a display device to display tomographic images generated by image generation unit 12 and image generation unit 12 generates tomographic images at corresponding positions from the three-dimensional image V1 and the three-dimensional comparison image V2. This allows comparative image reading using images accurately aligned based on each vertebra, thereby contributing to accurate image reading.

Further, in the first embodiment, as image generation unit 12 generates a plurality of tomographic images at corresponding positions along the central axes, a plurality of tomographic images at corresponding positions may be comparably displayed along the central axis. This allows easy understanding of the position on the spine of displayed tomographic images and easy comparative image reading of tomographic images of vertebrae along the vertebra central axis in series, whereby image reading efficiency may be improved.

As a second embodiment, a modification of the method performed by alignment unit 17 for aligning the third characteristic amount calculated from the three-dimensional image V1 with the third characteristic amount calculated from the three-dimensional comparison image V2 will now be described. The configuration and processing of each functional block are identical to those of each functional block of the first embodiment other than the method performed by alignment unit 17 for aligning the third characteristic amount calculated from the three-dimensional image V1 with the third characteristic amount calculated from the three-dimensional comparison image V2.

In the second embodiment, a squared sum of the difference between a third characteristic amount at each position z' on a central axis Z1 of a three-dimensional image V1 and a third characteristic amount at a position z'+$S_{z'}$, which is the position shifted by a shift amount of $S_{z'}$, from the position z' on a central axis Z2 of a three-dimensional comparison image V2 is minimized for each position z' on a central axis Z1 of a three-dimensional image V1 to obtain a shift amount $S_{z'}$ at each minimized position by a dynamic programming method, instead of the SSD method. More specifically, a shift amount that minimizes an evaluation function of formula (5) given below.

$$\min_{s_{z'}} \arg \sum_{z'=0}^{Z'} (f_{32}(z' + s_{z'}) - f_{31}(z'))^2 \quad (5)$$

According to this method, with respect to each position z' within the range of 0≤z'≤Z', a shift amount $S_{z'}$, that best matches the third characteristic amount of the three-dimensional image V1 with the third characteristic amount of the three-dimensional comparison image V2 may be calculated.

That is, the position corresponding to each position z' on the central axis of the three-dimensional image V1 may be calculated as the position z'+$S_{z'}$, on the central axis of the three-dimensional comparison image V2 that minimizes the evaluation function.

According to the second embodiment, the position on the central axis of the three-dimensional comparison image where the third characteristic amount of the three-dimensional image best matches with the third characteristic amount of the three-dimensional comparison image may be calculated with respect to each position on the central axis of the three-dimensional image. Thus, the position on the central axis of the three-dimensional comparison image corresponding to each position on the central axis of the three-dimensional image may be accurately calculated.

As a third embodiment, a modification of display control unit 18 will be described hereinafter. The configuration and processing of each functional block are identical to those of each functional block in the first embodiment other than the processing performed by display control unit 18 for displaying tomographic images.

Figure 10:
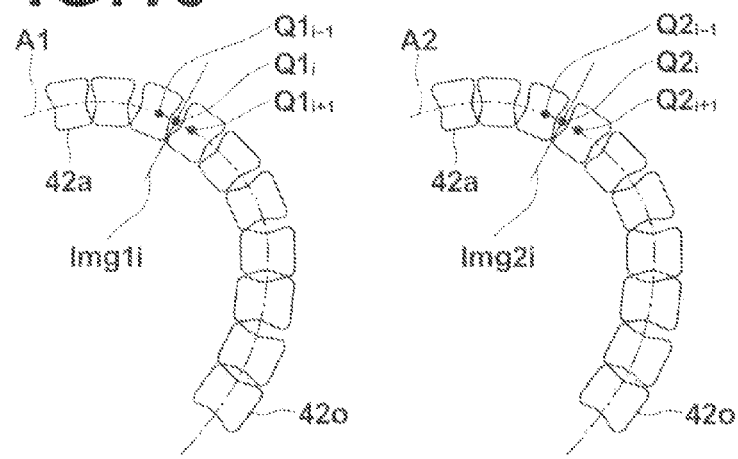
FIG. 10 illustrates corresponding positions on vertebra center lines of a three-dimensional image and a three-dimensional comparison image of a third embodiment.

As the third embodiment, display control unit 18 displays tomographic images (second tomographic images) orthogonal to the central axes at each position along the central axes. FIG. 10 schematically illustrates a sagittal image of a three-dimensional image V1 of a subject having a totally curve deformed spine and a corresponding sagittal image of a three-dimensional comparison image V2. It is assumed that the three-dimensional image V1 was obtained by CT imaging a subject several days before comparative image reading is performed while the three-dimensional comparison image V2 was obtained by CT imaging the same subject several months before the comparative image reading is performed.

In the third embodiment, processing of S01 to S08 shown in FIG. 3A is identical to that in the first embodiment. That is, three-dimensional images V1 and V2 are obtained, first tomographic images along a body axis direction are obtained with respect to each of the three-dimensional images V1 and V2, vertebral center lines A1 and A2 are detected, second tomographic images along the vertebra center lines are generated, first to third characteristic amounts are obtained at each point on the central axes A1 and A2, and the position of the third characteristic amount calculated from the three-dimensional image is aligned with the position of the third characteristic amount calculated from the three-dimensional comparison image V2. Then, a position $P2_i$ (0≤i<n) on $Z_2'$ axis of the three-dimensional comparison image V2 corresponding to a position $P1_i$ (0≤i<n) on $Z_1'$ axis of the three-dimensional image V1 is calculated, and $Q1_i$ and $Q2_i$ (0≤i<n) which are positions in an XYZ coordinate system obtained by converting the position $P1_i$ (0≤i<n) on $Z_1'$ axis of the three-dimensional image V1 and position $P2_i$ (0≤i<n) on $Z_2'$ axis of the three-dimensional comparison image V2 respectively. It is assumed here that n positions $P1_i$ (0≤i<n, i and n are positive integers) are sequentially set at an interval α on the central axis $Z_1'$ of the three-dimensional image V1 within the range 0≤z'≤Z' from the cervical vertebrae toward caudal vertebrae.

Then, as the processing of S09 in the third embodiment, display control unit 18 generates a tomographic image $Img1_i$, which includes a position $Q1_i$ (0≤i<n) on the central axis of the three-dimensional image V1 and orthogonal to the central axis A1 and a tomographic image $Img1_2$, which includes a position $Q2_i$ (0≤i<n) on the axis $Z_2'$ of the three-dimensional comparison image V2 and orthogonal to the central axis A2.

In the third embodiment, a normal line direction of the tomographic image $Img1_i$ orthogonal to the central axis A1 of the three-dimensional image V1 is obtained using coordinates $Q_{i-1}$, $Q_{i+1}$ adjacent to $Q1_i$ along the Z' axis. More specifically, display control unit 18 generates a plane that includes the position $Q1_i$ and has a normal line direction in a vector direction from the coordinate $Q1_{i-1}$ to $Q_{i+1}$ in the XYZ coordinate system as the tomographic image $Img1_i$ orthogonal to the central axis A1 of the three-dimensional image V1. The tomographic image $Img2_i$ orthogonal to the central axis A2 of the three-dimensional comparison image V2 may also be generated in the same manner as described above as a plane that includes the position $Q2_i$ and has a normal line direction in a vector direction from the coordinate $Q2_{i-1}$ to $Q2_{i+1}$. As for tomographic image $Img1_i$ or $imag2_i$ orthogonal to the central axis A1 of the three-dimensional image V1 or orthogonal to the central axis A2 of the three-dimensional comparison image V2, if the second tomographic images obtained in step S3 already include tomographic images that include each $Q1_i$ or $Q2_i$ (0≤i<n), the second tomographic images that includes each $Q1_i$ or $Q2_i$ (0≤i<n) may be used as the $Img1_i$ or $Img2_i$.

In the third embodiment, as in the first embodiment, with respect to the calculated corresponding positions $Q1_i$ and $Q2_i$ (0≤i<n) on the central axes of the three-dimensional image V1 and the three-dimensional comparison image V2, a pair of tomographic image $Img1_i$, which includes $Q1_i$ of the three-dimensional image V1 and orthogonal to the center line A1, and tomographic image $Img2_i$, which includes $Q2_i$ of the three-dimensional comparison image V2 and orthogonal to the center line A2, is generated based on the positions in the XYZ coordinate system (S09).

Figure 11:
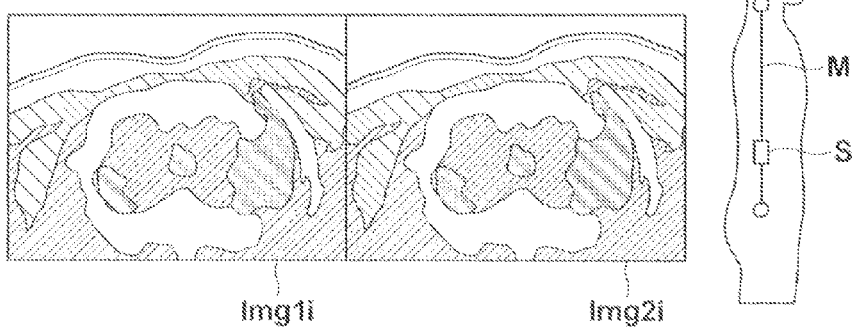
FIG. 11 illustrates an example display screen, showing tomographic images at the corresponding positions of the three-dimensional image and the three-dimensional comparison image of the third embodiment.

FIG. 11 illustrate an example image display in which a tomographic image Img1$_i$ and a tomographic image Img2$_i$ at corresponding positions to each other are comparably displayed. Finally, as in S10 in FIG. 3, display control unit 18 comparably displays the tomographic images Img1$_i$ and Img2$_i$ at corresponding positions, as illustrated in FIG. 11. In FIG. 11, the display range of tomographic images Img1$_i$ and Img2$_i$ at corresponding positions is limited to the cross-section of a vertebra with an intention to perform comparative image reading for a vertebral problem, the display range of tomographic images comparably displayed may be set arbitrarily as long as the tomographic images include the cross-section of the vertebra and, for example, a range that entirely covers an abdominal region of the subject may be set as the display range.

As in the first embodiment, also in the third embodiment, display control unit 18 is designed to receive an instruction to start comparative image reading from the user through, for example, a button provided in GUI and to sequentially display a plurality pairs of tomographic images Img1$_i$ and Img2$_i$ (0≤i<n, i and n are positive integers) along the cervical vertebra center lines A1 and A2 of the three-dimensional image V1 and the three-dimensional comparison image V2 (S10).

According to the third embodiment, advantageous effects of image reading are improved greatly by using tomographic images orthogonal to the vertebra centre line as tomographic images at corresponding positions along the cervical vertebra center lines A1 and A2 of the three-dimensional image V1 and the three-dimensional comparison image V2, instead of axial images. In particular, for a patient having a curved spine, it is difficult to understand the positions of anatomical structures, such as internal organs, in the vertical direction by axial images in comparison with a patient having a normal spine because the body axis is curved from the vertical direction. But, as in the third embodiment, display of tomographic images orthogonal to the vertebra center line along the vertebra center line allows positions of anatomical structures, such as internal organs to be understood relatively easily because the relative positions between the vertebra center line and each anatomical structure, such as an internal organ, is basically maintained in such tomographic images. When observing a vertebral problem or the like, image diagnosis based on tomographic images orthogonal to vertebrae, so that the present embodiment may contribute to more accurate comparative image reading by displaying tomographic images orthogonal to the vertebra center line at corresponding positions aligned more accurately along the central axes.

Further, as a modification of the third embodiment, any cross-section may be reconstructed by MPR (multiplanar reconstruction) with reference to a corresponding position on Z' axis. With vertebrae which are less likely to be influenced by respiration, posture, and the like, as the base, the modification may perform a comparative display of any type of tomographic image desired by medical front based on corresponding positions accurately aligned on the vertebra center line and is useful.

A fourth embodiment relates, as a modification of alignment unit 17, to an alignment method in the case where third characteristic amounts are calculated for different ranges of the three-dimensional image V1 and the three-dimensional comparison image, such as the case where the three-dimensional image V1 and the three-dimensional comparison image V2 are images of different areas of a subject. The configuration and processing of each functional block are identical to those of each functional block of the first embodiment other than the alignment method performed by alignment unit 17.

Figure 12:
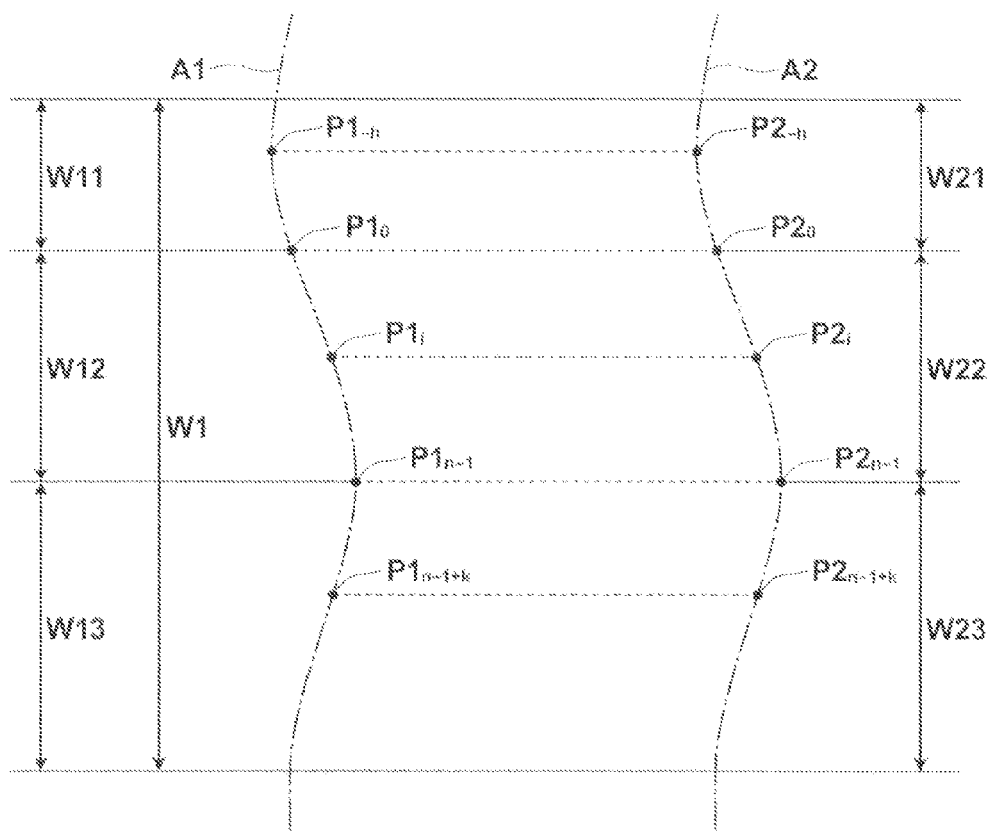
FIG. 12 illustrates corresponding positions on vertebra center lines of a three-dimensional image and a three-dimensional comparison image of a fourth embodiment.

In the fourth embodiment, it is assumed that the three-dimensional image V1 and the three-dimensional comparison image V2 are images of different areas of a patient. FIG. 12 illustrates center lines A1, A2 of the three-dimensional image V1 and the three-dimensional comparison image V2 in the fourth embodiment. As illustrated in FIG. 12, it is assumed that the imaging range W1 of the three-dimensional image V1 which includes vertebrae of the patient is greater in the body axis direction than the imaging range W22 of three-dimensional comparison image V2 which includes vertebrae of the patient.

First, medical image alignment apparatus 1 performs processing corresponding to steps S01 to S06 of the first embodiment in the same manner as the first embodiment, and extracts third characteristic amounts from the three-dimensional image Viand the three-dimensional comparison image V2 with respect to the entire range W1 of the three-dimensional image V1 and the range W22 of the three-dimensional comparison image V2.

Then, alignment unit 17, as the processing corresponding to S07 of the first embodiment, performs alignment with respect to an overlapping area along the central axis Z' of the three-dimensional image V1 and the three-dimensional comparison image V2 in the same manner as in the first embodiment. As illustrated in FIG. 12, if the imaging range W1 of the three-dimensional image V1 which includes a vertebra of the patient and imaging range W22 of the three-dimensional comparison image V2 which includes a vertebra of the patient are different, the three-dimensional image V1 and the three-dimensional comparison image are aligned with respect to the imaging range W12 of the imaging range W1 of the three-dimensional image V1 which includes a vertebra of the patient overlaps with the imaging range W22 of the three-dimensional comparison image V2 which includes a vertebra of the patient in the same method as that of the first embodiment. Then, with respect to the aligned area of W12, tomographic images at corresponding positions of the three-dimensional image V1 and the three-dimensional comparison image V2 are generated and displayed in the same manner as in steps S08 to S10 of the first embodiment.

According to the fourth embodiment, even when characteristic amounts are calculated with respect to different areas of the three-dimensional image V1 and the three-dimensional comparison image V2, the method of aligning third characteristic amounts according to the present invention may be applied as long as there is an overlapping area between the three-dimensional image V1 and the three-dimensional comparison image V2 for which a third characteristic amount is calculated. Then, by calculating the third characteristic amount for a necessary area of either the three-dimensional image V1 or the three-dimensional comparison image V2, the alignment method of the present embodiment may be applied, whereby calculation load may be reduced.

As a modification of the fourth embodiment, when a third characteristic amount is calculated only for a portion of an overlapping area of imaging range along each of the vertebra center lines A1, A2 of the three-dimensional image V1 and the three-dimensional comparison image V2, positions on the central axis Z' of the three-dimensional image V1 and the three-dimensional comparison image V2 may be related to each other using each shift amount calculated by the SSD method in the first embodiment or the dynamic programming in the second embodiment for a portion of either or both of the three-dimensional image V1 and the three-dimensional comparison image V2 where a third characteristic amount is not calculated in the overlapping area of imaging range along each of the vertebra center lines A, A2 of the three-dimensional image V1 and the three-dimensional comparison image V2.

For example, it is assumed, in FIG. 12, that the three-dimensional image V1 and the three-dimensional comparison image V2 are images taken with the same imaging range W1. It is also assumed that the third characteristic amount is calculated from the entire imaging range W1 for the three-dimensional image V1 while the third characteristic amount is calculated only from a partial range W22 of the imaging range W1 for the three-dimensional comparison image V2. Further, for the three-dimensional comparison image V2, it is assumed that, with respect to all of the ranges W21, W22, W23 constituting the imaging range W1, the center line A2 is extracted and an X' Y' Z' coordinate system along the center line A2 is set.

In this case, in the course of alignment processing, alignment unit 17 calculates first a shift amount $S_{zi}$ for each position $z_i'$ on the central axis Z' calculated by the dynamic planning in the second embodiment only for the range of W22 to calculate corresponding positions on the central axis Z' of the three-dimensional image V1 and the three-dimensional comparison image V2. Here, it is assumed that n positions $P1_i$ ($0 \le i < n$, i and n are positive integers) are sequentially set at an equal interval on the central axis $Z_1'$ of the three-dimensional image V1 within the range of W22 in the Z axis direction, i.e., within the range in the direction from the cervical vertebra toward coccyx vertebra. Then, with respect to each position $P1_i$ ($0 \le i < n$) on the central axis $Z_1'$ of the three-dimensional image V1, a position $P2_i$ (0, 0, $z_i' + S_{zi}$) on the central axis $Z_2'$ of the three-dimensional comparison image V2 corresponding to $P1_i$ (0, 0, $z_i'$) is obtained.

Then, a shift amount $S_{z0'}$ is calculated at position $P2_0$ on the central axis Z' and a shift amount $S_{zn-1'}$ is calculated at position $P2_{n-1}$ on the central axis Z'.

Here, in the modification of the fourth embodiment, with respect to the range W21 of three-dimensional comparison image V2 for which the third characteristic amount is not calculated, the position $P2_{-h}$ (0, 0, $z' + S_{z0'}$) on the central axis $Z_2'$ of the three-dimensional comparison image V2 is related to the position $P1_{-h}$ (0, 0, z') on the central axis of the three-dimensional image V1 as the position corresponding to the position $P1_{-h}$ (0, 0, z') using the shift amount $S_{z0'}$ at $P1_0$, as illustrated in FIG. 12. Likewise, with respect to the range W23 of three-dimensional comparison image V2 for which the third characteristic amount is not calculated, the position $P2_{n-1+k}$ (0, 0, $z' + S_{zn-1'}$) on the central axis $Z_2'$ of the three-dimensional comparison image V2 is related to the position $P1_{n-1+k}$ (0, 0, z') on the central axis of the three-dimensional image V1 as the point corresponding to the position $P1_{n-1+k}$ (0, 0, z') using the shift amount $S_{zn-1'}$ at $P1_0$, as illustrated in FIG. 12.

As described above, even when alignment processing of the present invention is performed only for a portion of the three-dimensional image V1 and the three-dimensional comparison image V2 along the vertebra center lines A1, A2 based on the third characteristic amount calculated from the three-dimensional image V1 and third characteristic amount calculated from three-dimensional comparison image V2, the alignment may be performed relatively accurately even for a portion in either or both of the three-dimensional image V1 and the three-dimensional comparison image V2 where a third characteristic amount is not calculated by using a shift amount of the position on the central axis of three-dimensional comparison image V2 with respect to the position on the central axis of the three-dimensional image V1 calculated by the alignment processing of alignment unit 17.

Further, as in the modification of the fourth embodiment, a shift amount error may be reduced to a minimum by applying the shift amount $S_{z0'}$, at the position $P2_0$ on the central axis Z', which is a position on a boundary of the range in which alignment processing is performed using the third characteristic amounts, to the range W21, which is a range closer to $P2_0$ of the ranges W21, W23 for which alignment processing is not performed and applying the shift amount $S_{zn-1'}$ at the position $P2_{n-1}$ on the central axis Z', which is a position on a boundary of the range in which alignment processing is performed using the third characteristic amounts, to the range W23, which is a range closer to $P2_{n-1}$ of the ranges W21, W23 for which alignment processing is not performed. Further, a neck portion and a portion from the waist downward are less likely to be changed in length with time by gravity force, so that it can be said that the shift amount at the boundary may well be used. In the case where alignment of positions on the center lines of the three-dimensional image V1 and the three-dimensional comparison image V2 is performed by the SSD method, as in the first embodiment, the position $P2_{-h}$ (0, 0, $z' + s$) on the central axis $Z_2'$ of the three-dimensional comparison image V2 may be related to the position $Ph_{-h}$ (0, 0, z') on the central axis of the three-dimensional image V1 as the position corresponding to the position $P1_{-h}$ (0, 0, z') and the position $P2_{n-1+k}$ (0, 0, $z' + s$) on the central axis $Z_2'$ of the three-dimensional comparison image V2 may be related to the position $P1_{n-1+k}$ (0, 0, z') on the central axis of three-dimensional image V1 using shift amount s for the ranges W21, W23 of the three-dimensional comparison image V2 for which a third characteristic is not calculated, as illustrated in FIG. 12.

Medical image alignment apparatus 1 may be configured by a plurality of computers to share the functions of image obtaining unit, image generation unit, vertebra centerline detection unit, first characteristic amount calculation unit, second characteristic amount calculation unit, third characteristic amount calculation unit, alignment unit, and display control unit. Further, devices constituting the system, such as input device, display, and the like, any known device may be used. For example, a joy stick may be used instead of the mouse and a touch panel may be used instead of the display.

In each of the embodiments described above, the three-dimensional image V1 and the three-dimensional comparison image V2 are aligned and a plurality of pairs of tomographic images at corresponding positions is generated and stored inside of medical image alignment apparatus 1 first, and then user specification of the position on the center line is received and tomographic images of the three-dimensional image V1 and the three-dimensional comparison image V2 corresponding to the specified position are displayed. In this case, display processing may be performed rapidly as all of tomographic image pairs for comparative image reading are generated in advance. But the start timing of the medical image alignment processing is not limited to this and various timings may be possible. For example, when performing image reading of tomographic images of the three-dimensional image V1, a user-selectable alignment button may be displayed on the GUI, then the three-dimensional comparison image V2 may be obtained from a server (not shown) by user clicking of the alignment button with an input device, such as the mouse or the like, and one of the medical image alignment processing in the aforementioned embodiments may be initiated.

The three-dimensional image may be any type of three-dimensional image as long as the first, second, and third characteristic amounts of the present invention can be calculated and a three-dimensional image obtained by CT imaging is preferably used.

Figure 13:
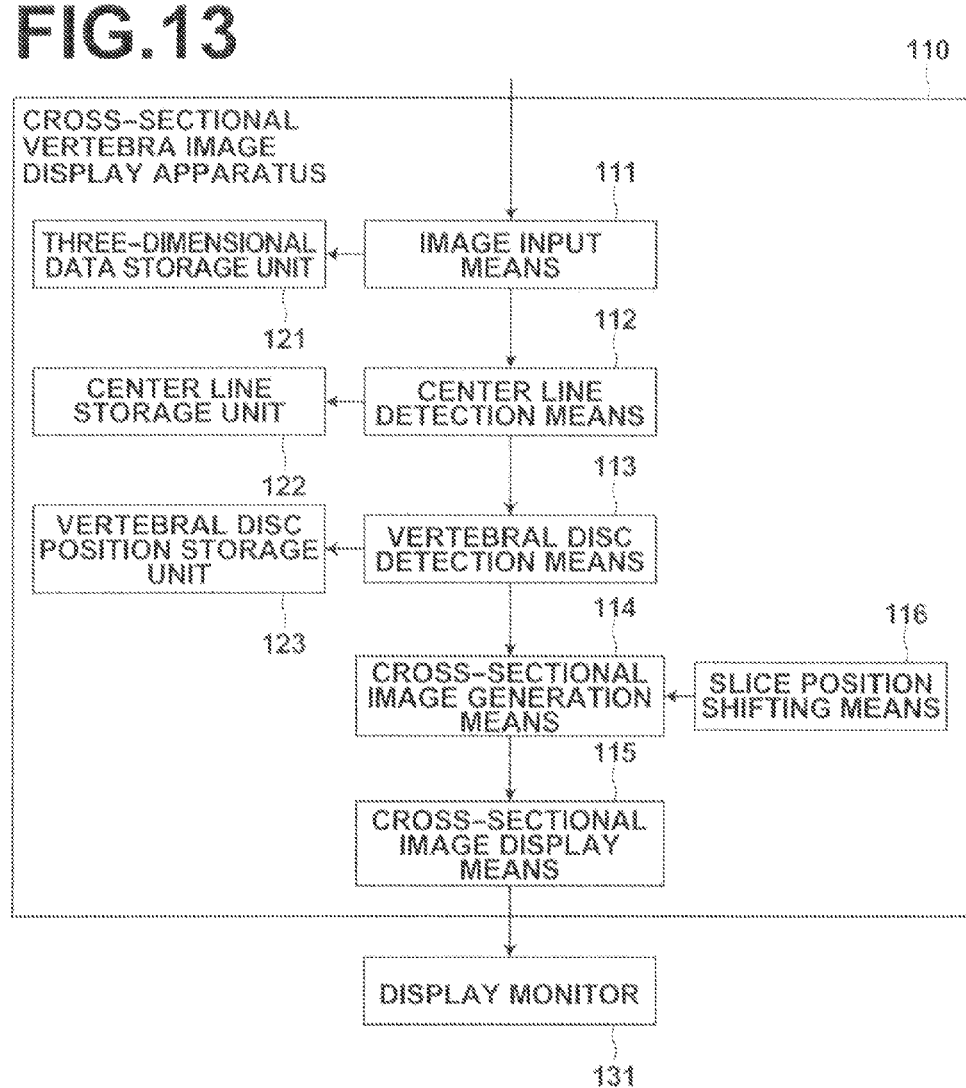
FIG. 13 is a block diagram of a cross-sectional vertebra image display apparatus according to an embodiment of the present invention.

Hereinafter, a fifth embodiment of the present invention will be described in detail with reference to the accompanying drawings. FIG. 13 illustrates a cross-sectional vertebra image display apparatus according to the fifth embodiment. Cross-sectional vertebra image display apparatus 110 includes image input means 111, center line detection means 112, vertebral disc detection means 113, cross-sectional image generation means 114, cross-sectional image display means 115, and slice position shifting means 116. The function of each unit of cross-sectional vertebra image display apparatus 110 can be realized by a computer that performs processing according to a predetermined program.

Image input means 111 inputs three-dimensional image data (hereinafter, also simply referred to as three-dimensional data) which include a vertebra and stores the data in three-dimensional data storage unit 121. Center line detection means 112 detects a center line along the shape of vertebrae based on the three-dimensional data and stores information of the detected center line in center line storage unit 122. Vertebral disc detection means 113 detects the position of a vertebral disc between adjacent vertebral bodies based on the three-dimensional data and stores position information of the detected vertebral disc in vertebral disc position storage unit 123.

Cross-sectional image generation means 114 refers to three-dimensional data storage unit 121 and center line storage unit 122, and generates a cross-sectional image of a vertebra sliced orthogonal to the center line based on the three-dimensional data. With a plurality of positions on the vertebra center line as slice positions, cross-sectional image generation means 114 generates a plurality of cross-sectional images of vertebrae sliced by planes orthogonal to the center line passing the slice positions. Cross-sectional image display means 115 displays the plurality of cross-sectional images generated at the plurality of slice positions side by side on the display screen of display monitor 31.

Slice position shifting means 116 shifts a slice position of a cross-sectional image generated by cross-sectional image generation means 114 along the vertebra center line. For example, slice position shifting means 116 jointly shifts slice positions of a plurality of cross-sectional images along the vertebra center line. In other words, slice position shifting means 116 shifts slice positions of a plurality of cross-sectional images in synchronization with each other along the vertebra center line. If slice positions are shifted by slice position shifting means 116, cross-sectional image generation means 114 generates a cross-sectional image of a vertebra sliced by a plane orthogonal to the center line at each shifted slice position.

Figure 14:
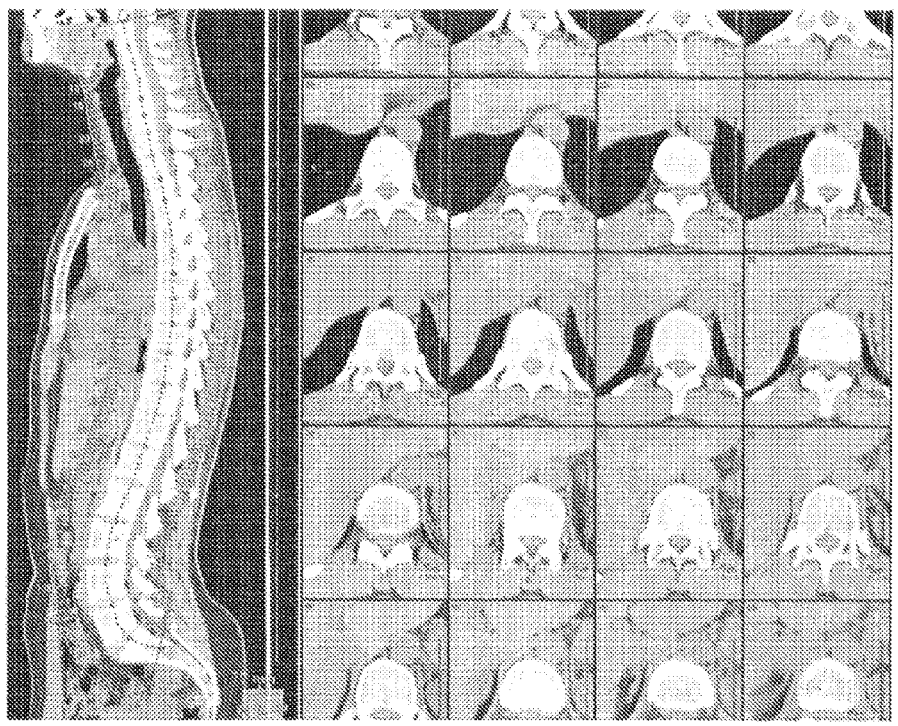
FIG. 14 shows an example screen display.

FIG. 14 shows an example screen display. The left side of the display screen is an area in which the cross-sectional image of the entire vertebrae is displayed. The right side of the display screen is an area in which a cross-sectional image at the position of a vertebral body or a vertebral disc constituting each vertebra. For example, cross-sectional image display means 115 displays cross-sectional images of all of the vertebral bodies or vertebral discs side by side on the display screen. Otherwise, cross-sectional image display means 115 may display cross-sectional images of some of the vertebral bodies or vertebral discs constituting vertebrae side by side. For example, cross-sectional image display means 115 may display cross-sectional images of cervical vertebrae or lumbar vertebrae side by side.

Figure 15:
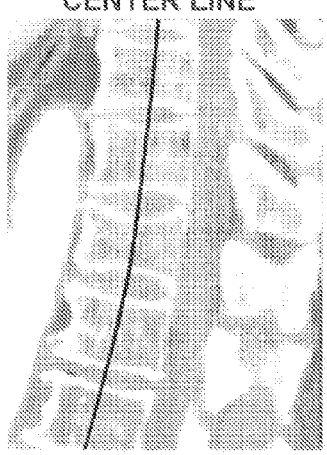
FIG. 15 illustrates a detected center line.

FIG. 15 illustrates a detected center line. Center line detection means 112 detects a line passing through substantially the center of each vertebral body constituting each vertebra as the center line. Any method may be used for the detection of vertebra center line. The detection of vertebra center line may be performed manually. Further, the detection of center line is not necessarily performed in cross-sectional vertebra image display apparatus 110, and it is possible to input center line information from outside together with three-dimensional data. The term "center line" is used herein for convenience, but the vertebra center line may be any line as long as it follows the shape of vertebrae and not necessarily the line passing through the center of vertebrae.

FIG. 16 illustrates positions of detected vertebral discs. For example, vertebral disc detection means 113 detects a position between adjacent vertebral bodies as a vertebral disc. Also for the detection of vertebral discs, any method may be used. The detection of vertebral discs may be performed manually. Further, the detection of vertebral discs is not necessarily performed in cross-sectional vertebra image display apparatus 110, and it is possible to input vertebral disc information from outside together with three-dimensional data.

Slice position shifting means 116 may provide a position between adjacent vertebral bodies, i.e., a position of a vertebral disc to cross-sectional image generation means 114 as an initial slice position. Further, slice position shifting means 116 may set a coordinate along the center line between adjacent vertebral discs and shift the slice position according to the coordinate. In this case, slice position shifting means 116 may perform the coordinate setting according a distance between adjacent vertebral discs on the vertebra center line. For example, slice position shifting means 116 may divide a distance between adjacent vertebral discs on the vertebra center line by a predetermined division number, and each divided position on the center line may be regarded as a coordinate position (slice point) that can be a slice position.

FIG. 17 illustrate an example coordinate setting. In FIG. 17, the vertebra center line is represented by a straight line. Here, three vertebral discs of vertebral vertebral $disc_i$, and vertebral $disc_{i+1}$ (i is an arbitrary natural number) are considered. The distance from the vertebral $disc_{i-i}$ to vertebral $disc_i$ on the center line is assumed to be $d_{i-1}$ and the distance from the vertebral $disc_i$ to vertebral $disc_{i+1}$ on the center line is assumed to be $d_i$. Here the division number assumed is 5. With the position of vertebral $disc_{i-i}$ as the coordinate position 0, slice position shifting means 116 dives the distance from the coordinate position 0 to the position of vertebral $disc_i$ by 5 to set each divided position as coordinate positions 1, 2, 3, and 4. Likewise, with the position of vertebral $disc_i$ as the coordinate position 0, slice position shifting means 116 divides the distance $d_i$ between the vertebral $disc_i$ to vertebral $disc_{i+1}$ by 5 to set each divided position as coordinate positions 1, 2, 3, and 4. The coordinate setting method described above is merely an example and not limited to this.

In the initial state, cross-sectional image generation means 114 generates a cross-sectional image at each vertebral disc, i.e., at each coordinate position 0. When a user operation to advance slice positions is performed, slice position shifting means 116 changes each slice position from coordinate position 0 to coordinate position 1. Cross-sectional image generation means 114 generates cross-sectional images by shifting the slice positions to coordinate positions 1. In the aforementioned case, cross-sectional image generation means 114 generates cross-sectional images, for the vertebral at the position advance by $d_{i-1}/5$ from the position of vertebral and generates a cross-sectional image, for the vertebral $disc_i$, at the position advance by $d_i/5$ from the position of vertebral $disc_i$. By shifting the coordinate position with respect to the position of each vertebral disc in synchronization with each other, the position of cross-section displayed in each cross-sectional image may by jointly shifted.

Here, if the position of each vertebral disc is represented as 0% and the position of an adjacent vertebral disc is represented as 100%, the coordinate positions 1, 2, 3, and 4 may be represented as the positions of 20%, 40%, 60%, and 80% respectively. When such coordinate setting as described above is performed, positions on the center line (slice points) which can be slice positions are set discretely as the positions of 20%, 40%, 60%, and 80%. Instead of discretely setting the slice points, it is possible to arbitrarily set a slice position from 0% to 100% for each of a plurality of cross-sectional images.

Figure 18:
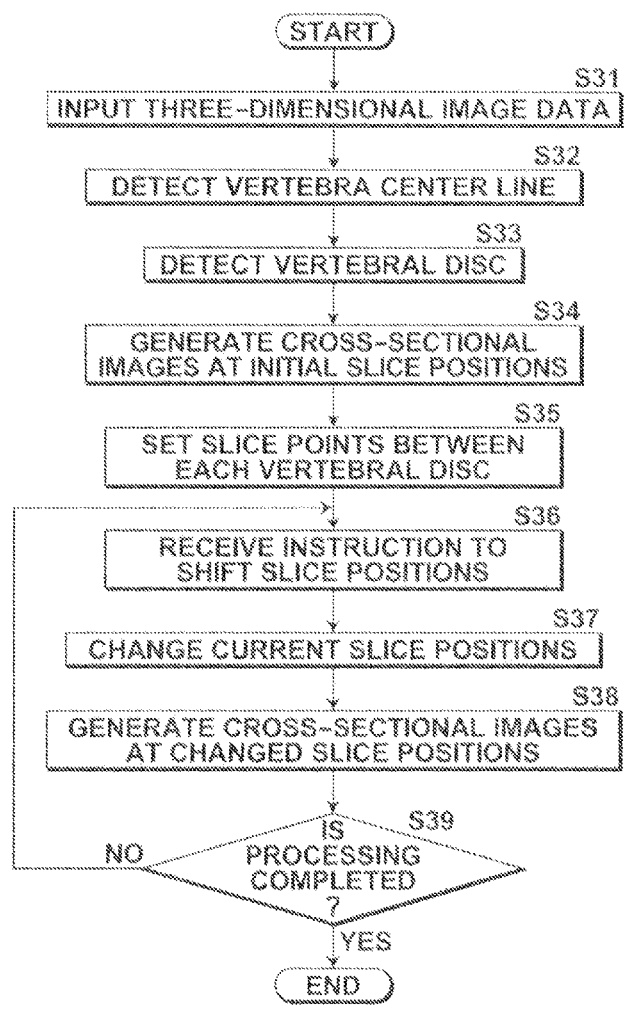
FIG. 18 is a flowchart illustrating an operation procedure.

FIG. 18 is a flowchart illustrating an operation procedure. Image input means 111 inputs three-dimensional data and stores the data in three-dimensional data storage unit 121 (step S31). Center line detection means 112 detects a vertebra center line based on the three-dimensional data and stores information of the detected center line in center line storage unit 122 (step S32). Vertebral disc detection means 113 detects the position of a vertebral disc based on the three-dimensional data and stores position information of the detected vertebral disc in vertebral disc position storage unit 123 (step S33). If the center line information and position information of vertebral disc are given from outside, steps S32, S33 may be omitted.

With each vertebral disc position as the initial slice position, cross-sectional image generation means 114 generates a cross-sectional image of vertebra sliced by a plane orthogonal to the center line passing the initial slice position (step S34). The initial slice position may be set by slice position shifting means 116. The slice surface of the cross-sectional image generated by cross-sectional image generation means 114 is not necessarily orthogonal to the vertebra center line in a strict sense and may be slightly deviated from right angle. Cross-sectional image display means 115 displays generated cross-sectional images on the display screen of display monitor 131 side by side.

Slice position shifting means 116 sets a coordinate between adjacent vertebral discs (step S35). In step S35, slice position shifting means 116 sets coordinate positions (slice points) that can be slice positions between each vertebral disc. Slice position shifting means 116 sets the same number of slice points between each vertebral disc regardless of the distance to an adjacent vertebral disc. Slice position shifting means 116 sets, for example, five slice points, including the initial slice position, between each vertebral disc.

Slice position shifting means 116 receives an instruction to shift the slice positions (step S36). The user may instruct shifting of slice positions, for example, by rotating a mouse wheel. When an instruction to shift slice positions is given by the user, slice position shifting means 116 shifts the current slice positions to different slice positions (step S37). Here, slice position shifting means 116 shifts each slice position to any one of the coordinate positions set in step S35. For example, slice position shifting means 116 shifts the slice position of each cross-sectional image to each corresponding coordinate position.

Cross-sectional image generation means 114 generates cross-sectional images at shifted slice positions (step S38). Cross-sectional image display means 115 displays cross-sectional images at the changed slice positions on the display screen of display monitor 31 side by side. Slice position shifting means 116 determines whether or not the processing is completed (step S39). If the processing is not completed, slice position shifting means 116 returns to step S36 and receives an instruction to shift slice positions. Slice position shifting means 116 shifts slice positions every time an instruction to shift slice positions is received from the user, and cross-sectional image generation means 114 generates cross-sectional images at the shifted slice positions. When a determination is made in step S39 that the processing is completed, the processing is terminated.

Figure 19:
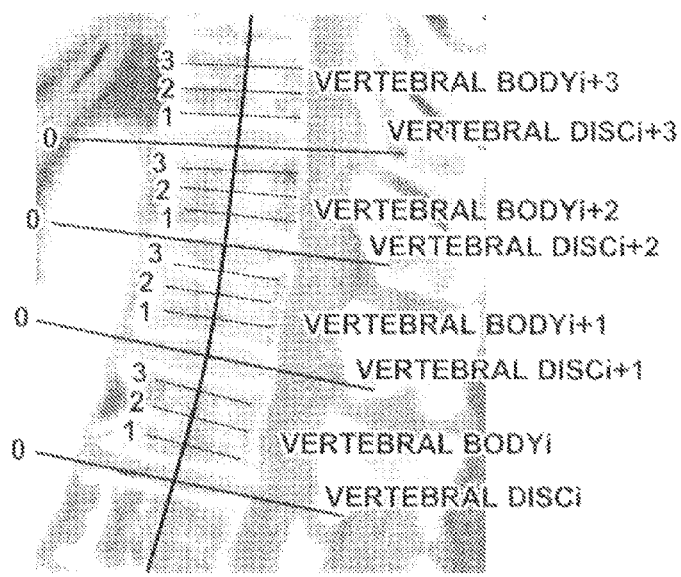
FIG. 19 illustrates a specific example of a coordinate position set between adjacent vertebral discs.

FIG. 19 illustrate an example of specific coordinate positions set in step S35. Here, four vertebral discs from vertebral disc$_i$ to vertebral disc$_{i+3}$ are considered. The vertebral body between vertebral disc$_i$ and vertebral disc$_{i+1}$ is referred to as vertebral body$_i$, vertebral body between vertebral disc$_{i+1}$ and vertebral disc$_{i+2}$ is referred to as vertebral body$_{i+1}$, vertebral body between vertebral disc$_{i+2}$ and vertebral disc$_{i+3}$ is referred to as vertebral body$_{i+2}$, and vertebral body between vertebral disc$_{i+3}$ and vertebral disc$_{i+4}$ (not shown) is referred to as vertebral body$_{i+3}$. Slice position shifting means 116 divides the distance between adjacent vertebral discs into four and sets coordinate position 1, coordinate positions 2, and coordinate position 3 between adjacent vertebral discs (each vertebral body).

Figure 20A:
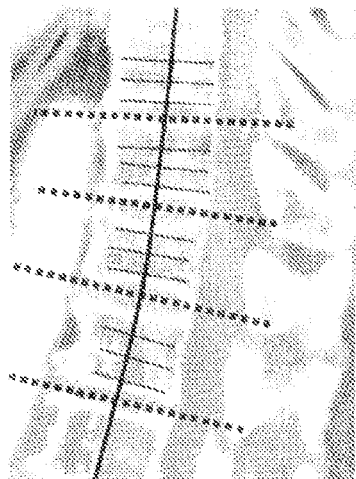
FIG. 20A illustrates initial slice positions.
Figure 20B:
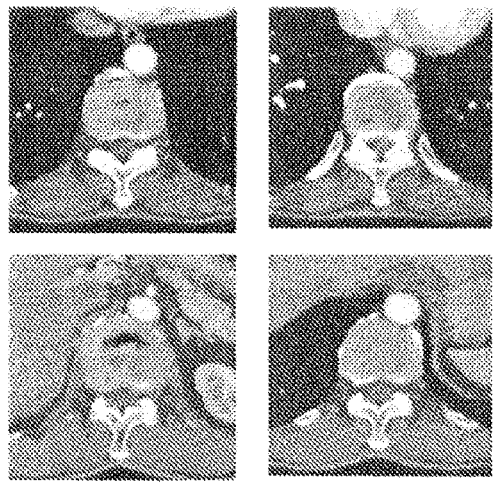
FIG. 20B illustrates cross-sectional images at the initial slice positions.

FIG. 20A illustrates initial slice positions, and FIG. 20B illustrates cross-sectional images at the initial slice positions. In step S34, cross-sectional image generation means 114 generates cross-sectional images at vertebral disc positions of initial slice positions. The initial slice positions are illustrated by dotted lines in FIG. 20. The initial slice positions correspond to each coordinate position 0 in FIG. 19. Cross-sectional image display means 115 displays cross-sectional images at four vertebral disc positions side by side. The user may diagnose if there is any trouble by comparing and examining the displayed cross-sectional images.

Figure 21A:
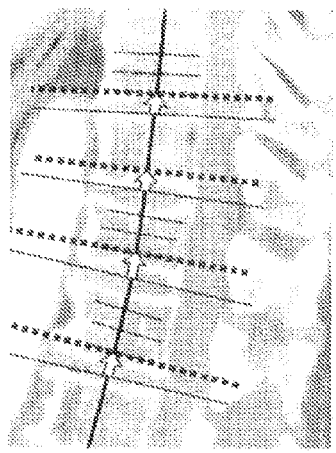
FIG. 21A illustrates shifted slice positions.
Figure 21B:
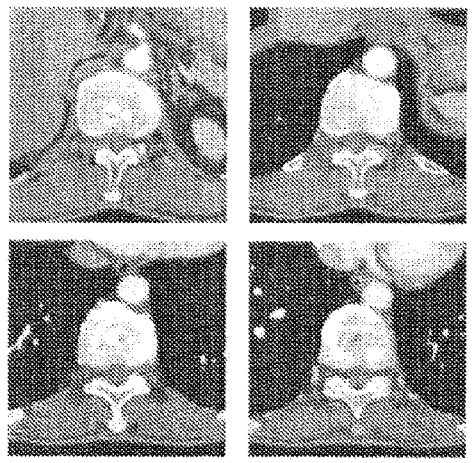
FIG. 21B illustrates cross-sectional images at the shifted slice positions.

In step S36, if an instruction to change the slice positions is given by the user, slice position shifting means 116 shifts slice positions from the initial slice position to, for example, each coordinate position 1 in FIG. 19. FIG. 21A illustrates shifted slice positions and FIG. 21B illustrates cross-sectional images at the shifted slice positions. As illustrated in FIG. 21A, slice position shifting means 116 shifts slice positions from the position of each vertebral disc to each coordinate position 1. Cross-sectional image generation means 114 generates four cross-sectional images at the shifted slice positions, and cross-sectional image display means 115 displays four generated cross-sectional images side by side, as illustrated in FIG. 21B.

Figure 22A:
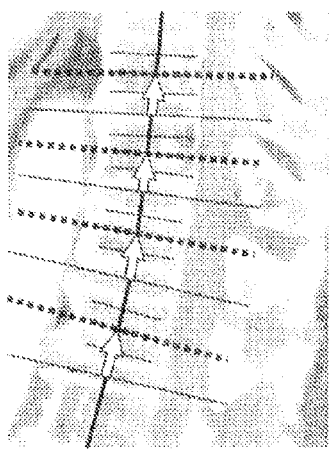
FIG. 22A illustrates further shifted slice positions.
Figure 22B:
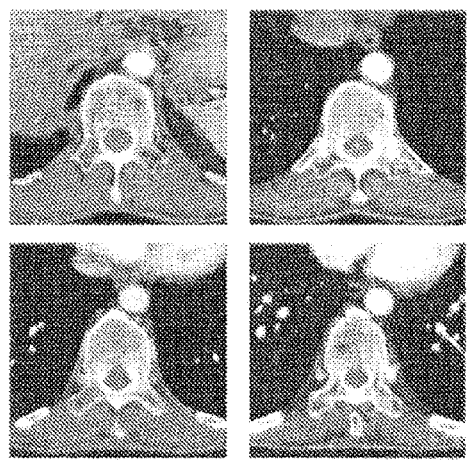
FIG. 22B illustrates cross-sectional images at the further shifted slice positions.

When slice positions are further changed by the user, slice position shifting means 116 shifts the current slice positions to, for example, each coordinate position 2 in FIG. 19. FIG. 22A illustrated further shifted slice positions and FIG. 22B illustrates cross-sectional images at the further shifted positions. As illustrated in FIG. 22A, slice position shifting means 116 shifts slice positions to each coordinate position 2. Cross-sectional image generation means 114 generates four cross-sectional images at the shifted slice positions, and cross-sectional image display means 115 displays four generated cross-sectional images side by side, as illustrated in FIG. 22B. The user may arbitrarily shift the slice position from coordinate position 0 to coordinate position 3. The cross-sectional image at each slice position may be displayed as a moving image, like an animation. The user may examine cross-sectional images at any desired coordinate positions by arbitrarily shifting the slice positions.

In the fifth embodiment, slice position shifting means 116 shifts slice positions at which cross-sectional image generation means 114 generates a plurality of cross-sectional images along the vertebra center line. Cross-sectional image generation means 114 generates a plurality of cross-sectional images of vertebrae at the shifted slice positions and cross-sectional image display means 115 displays the plurality of generated cross-sectional image side by side. This allows the user to examine a cross-section of vertebra at any position on the vertebra center line. In the case where slice position shifting means 116 is configured to jointly shift slice positions of a plurality of cross-sectional images along the vertebra center line, slice positions of a plurality of cross-sectional images displayed side by side may be shifted simultaneously.

In the mean time, it can be said that when a vertebral fracture or the like occurs, the vertebral body becomes smaller than other vertebral bodies. Cross-sectional image display means 115 may be configured to identify a position where a vertebral body size is not greater than a predetermined reference value and to highlight the cross-sectional image corresponding to the identified position. Determination as to whether or not the size of a vertebral body is smaller than a reference value may be made, for example, by comparing the distance between adjacent vertebral bodies to a predetermined threshold value. Otherwise, each distance between adjacent vertebral discs may be compared and the position where the distance between adjacent vertebral discs is smaller than that of other adjacent vertebral discs may be identified as the position where the size of the vertebral body is smaller than the reference value.

Figure 23A:
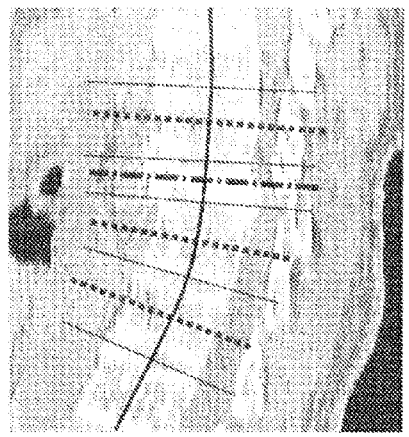
FIG. 23A illustrates a vertebral compression fracture.
Figure 23B:
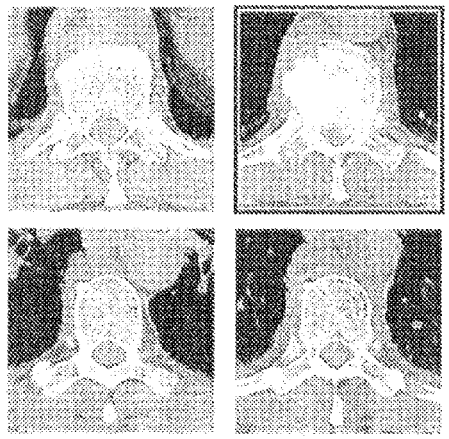
FIG. 23B illustrates an example display of cross-sectional images having a vertebral compression fracture.

FIG. 23A illustrates a vertebral compression fracture and FIG. 23B illustrates an example display of cross-sectional images having a vertebral compression fracture. Cross-sectional image display means 115 detects a position where the distance between adjacent vertebral discs is smaller than the distances around and, for example, the position where the distance between the adjacent vertebral discs is smaller may be highlighted in red, as illustrated in FIG. 23A. Further, a cross-sectional image corresponding to the position where the distance between adjacent vertebral discs is smaller may be highlighted by, for example, encircling the image with a red line, as illustrated in FIG. 23B. This allows the user to easily find a position having a vertebral compression fracture.

In the fifth embodiment, the description has been made of a case in which positions of vertebral discs are detected and slice positions are determined with reference to the detected positions, but not limited to this. For example, each vertebral body constituting each vertebra may be detected from three-dimensional data and slice positions may be determined based on the position of each detected vertebral body. For example, slice position shifting means 116 may determines the center position of each vertebral body to be the initial slice position, set a coordinate between adjacent vertebral bodies according to the distance between the centers of adjacent vertebral bodies, and shift the slice position from the initial slice position according to the coordinate.

The shifting range of the slice position is not limited to the distance between adjacent vertebral bodies and may be set arbitrarily. For example, in the case where the position of vertebral disc$_i$ (FIG. 17) is used as the initial slice position, a coordinate may be set between a position a certain distance away from the vertebral disc$_i$ on the side of vertebral disc$_{i-1}$ and a position a certain distance away from the vertebral disc$_i$ on the side of vertebral disc$_{i+1}$ and slice positions may be shifted between the two positions. In this case, for example, the position of the vertebral disc$_i$ may be defined as coordinate position 0, and a position in the vertebral disc$_{i-1}$ side is defined as a negative coordinate position while a position in the vertebral disc$_{i+1}$ side is defined as a positive coordinate position.

It should be appreciated that the present invention is not limited the embodiments described above and may vary within the spirit and scope of the present invention.

What is claimed is:

1. A medical image alignment apparatus for aligning a three-dimensional image which represents a subject having vertebrae with a three-dimensional comparison image for being compared with the three-dimensional image, wherein the three-dimensional comparison image represents the subject and is a different image from the three-dimensional image, the apparatus comprising:
 a three-dimensional image detector configured to obtain the three-dimensional image and the three-dimensional comparison image;
 an image generator configured to generate, with respect to each of the three-dimensional image and the three-dimensional comparison image, a plurality of tomographic images orthogonal to a central axis of each vertebra of the subject along the central axis;
 a first characteristic amount calculation processing unit configured to calculate, with respect to each of the three-dimensional image and the three-dimensional comparison image, a first characteristic amount representing a profile in a direction orthogonal to the central axis at each point on the central axis based on the tomographic images;
 a second characteristic amount calculation processing unit configured to calculate, with respect to each of the three-dimensional image and the three-dimensional comparison image, a second characteristic amount representing a profile in a direction of the central axis at each point on the central axis based on the tomographic images;
 a third characteristic amount calculation processing unit configured to calculate, with respect to each of the three-dimensional image and the three-dimensional comparison image, a third characteristic amount representing regularity of disposition of each vertebra at each point on the central axis based on the calculated first and second characteristic amounts; and
 a vertebra alignment processing unit configured to align positions of the third characteristic amount calculated from the three-dimensional image and the third characteristic amount calculated from the three-dimensional comparison image along the central axis.

2. The apparatus of claim 1, wherein the first characteristic amount represents an annular pattern centered on each point on the central axis.

3. The apparatus of claim 1, wherein the second characteristic amount represents a disc shaped pattern that appears along the central axis.

4. The apparatus of claim 1, wherein vertebra processing alignment unit aligns the third characteristic amount calculated from the three-dimensional image with the third characteristic amount calculated from the three-dimensional comparison image using an SSD method.

5. The apparatus of claim 1, wherein vertebra alignment processing unit aligns the third characteristic amount calculated from the three-dimensional image with the third characteristic amount calculated from the three-dimensional comparison image using a dynamic planning method.

6. The apparatus of claim 1, wherein:
 the apparatus further comprises an image display control unit for causing a tomographic image generated by the image generation unit to be displayed on a display device; and
 the image generator generates, from the three-dimensional image and the three-dimensional comparison image, tomographic images at corresponding positions.

7. The apparatus of claim 6, wherein the tomographic images at corresponding positions are orthogonal to central axes extracted from the three-dimensional image and the three-dimensional comparison image respectively.

8. The apparatus of claim 6, wherein the image generator generates a plurality of pairs of tomographic images at corresponding positions along the central axis.

9. A medical image alignment method for aligning a three-dimensional image which represents a subject having vertebrae with a three-dimensional comparison image for comparison with the three-dimensional image, wherein the three-dimensional comparison image represents the subject and is a different image from the three-dimensional image, the method comprising the steps of:
   obtaining the three-dimensional image and the three-dimensional comparison image;
   generating, with respect to each of the three-dimensional image and the three-dimensional comparison image, a plurality of tomographic images orthogonal to a central axis of each vertebra of the subject along the central axis;
   calculating, with respect to each of the three-dimensional image and the three-dimensional comparison image, a first characteristic amount representing a profile in a direction orthogonal to the central axis at each point on the central axis based on the tomographic graphic images;
   calculating, with respect to each of the three-dimensional image and the three-dimensional comparison image, a second characteristic amount representing a profile in a direction of the central axis at each point on the central axis based on the tomographic images;
   calculating, with respect to each of the three-dimensional image and the three-dimensional comparison image, a third characteristic amount representing regularity of disposition of each vertebra at each point on the central axis based on the calculated first and second characteristic amounts; and
   aligning positions of the third characteristic amount calculated from the three-dimensional image and the third characteristic amount calculated from the three-dimensional comparison image along the central axis.

10. A non-transitory computer readable recording medium on which is recorded a medical image alignment program for aligning a three-dimensional image which represents a subject having vertebrae with a three-dimensional comparison image for comparison with the three-dimensional image, wherein the three-dimensional comaparison image represents the subject and is different from the three-dimensional image, the program causing a computer to function as:
   a three-dimensional image detector configured to obtaining the three-dimensional image and the three-dimensional comparison image;
   an image generator configured to generate, with respect to each of the three-dimensional image and the three-dimensional comparison image, a plurality of tomographic images orthogonal to a central axis of each vertebra of the subject along the central axis;
   a first characteristic amount calculation processing unit configured to calculate, with respect to each of the three-dimensional image and the three-dimensional comparison image, a first characteristic amount representing a profile in a direction orthogonal to the central axis at each point on the central axis based on the tomographic images;
   a second characteristic amount calculation processing unit configured to calculate, with respect to each of the three-dimensional image and the three-dimensional comparison image, a second characteristic amount representing a profile in a direction of the central axis at each point on the central axis based on the tomographic images;
   a third characteristic amount calculation processing unit configured to calculate, with respect to each of the three-dimensional image and the three-dimensional comparison image, a third characteristic amount representing regularity of disposition of each vertebra at each point on the central axis based on the calculated first and second characteristic amounts; and
   a vertebra alignment processing unit configured to align positions of the third characteristic amount calculated from the three-dimensional image and the third characteristic amount calculated from the three-dimensional comparison image along the central axis.

* * * * *